(12) United States Patent
Neumann

(10) Patent No.: US 9,394,337 B2
(45) Date of Patent: Jul. 19, 2016

(54) ION EXCHANGE CHROMATOGRAPHY WITH IMPROVED SELECTIVITY FOR THE SEPARATION OF POLYPEPTIDE MONOMERS, AGGREGATES AND FRAGMENTS BY MODULATION OF THE MOBILE PHASE

(71) Applicant: Hoffmann-La Roche Inc., Nutley, NJ (US)

(72) Inventor: Sebastian Neumann, Weilheim (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 230 days.

(21) Appl. No.: 14/025,622

(22) Filed: Sep. 12, 2013

(65) Prior Publication Data

US 2014/0081000 A1    Mar. 20, 2014

Related U.S. Application Data

(63) Continuation of application No. PCT/EP2012/054449, filed on Mar. 14, 2012.

(30) Foreign Application Priority Data

Mar. 16, 2011  (EP) .................................... 11158523

(51) Int. Cl.
| | |
|---|---|
| *C07K 1/18* | (2006.01) |
| *B01D 15/36* | (2006.01) |
| *A61K 39/395* | (2006.01) |
| *C07K 16/00* | (2006.01) |
| *C07K 16/22* | (2006.01) |
| *C07K 16/24* | (2006.01) |
| *C07K 16/28* | (2006.01) |
| *C07K 16/26* | (2006.01) |

(52) U.S. Cl.
CPC .............. *C07K 1/18* (2013.01); *A61K 39/39591* (2013.01); *C07K 16/00* (2013.01); *C07K 16/22* (2013.01); *C07K 16/244* (2013.01); *C07K 16/26* (2013.01); *C07K 16/2863* (2013.01); *C07K 16/2866* (2013.01); *B01D 15/362* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 2001/0051708 A1* | 12/2001 | Laursen et al. ............ | 530/387.1 |
| 2006/0003406 A1* | 1/2006 | Lee et al. ..................... | 435/69.1 |
| 2006/0247423 A1 | 11/2006 | Su et al. | |
| 2009/0187005 A1 | 7/2009 | Gagnon | |
| 2009/0240040 A1* | 9/2009 | Krishnamurthy et al. .... | 530/419 |

FOREIGN PATENT DOCUMENTS

| | | | |
|---|---|---|---|
| DE | 19836213 A1 * | 2/2000 | |
| WO | 99/64462 A1 | 12/1999 | |
| WO | 2004/013162 A2 | 2/2004 | |
| WO | 2005/094960 A1 | 10/2005 | |
| WO | 2006/125599 A2 | 11/2006 | |
| WO | 2008/086335 A2 | 7/2008 | |
| WO | 2009/149067 A1 | 12/2009 | |
| WO | 2010/148143 A1 | 12/2010 | |

OTHER PUBLICATIONS

Azevedo et al., "Downstream Processing of Human Antibodies Integration an Extraction Capture Step and Cation Exchange Chromatography" Journal of Chromatography B 877:50-58 ( 2009).
Gagnon et al., "Nonionic Polymer Enhancement of Aggregate Removal in Ion Exchange and Hydroxyapatite Chromatography" (12th Annual Waterside Conference, San Juan Puerto Rico), ( 2007).
Gagnon, "Monoclonal Antibody Purification with Hydroxyapatite" New Biotechnology :25(5):287-293 ( 2009).
Kumar et al., "Effect of Polyols on Polyethylene Glycol (PEG)-Induced Precipitation of Proteins: Impact on Solubility, Stability and Conformation" International Journal of Pharmaceutics 366:38-43 ( 2009).
Lu et al., Journal of Chromatography A 1059:233-237 ( 2004).
Paleg et al., "Proline and Glycine Betaine Influence Protein Solvation" Plant Physiology 75:974-978 ( 1984).
Sheng et al., "Polyethylene Glycol-Accompanied Ion-Exchange Chromatography to Purify Recombinant Hepatitis B Virus Surface Antigen" 21(6):947-953 ( 2005).
Snyder et al., "PEG Enhances Viral Clearance on Ceramic Hydroxyapatite" Journal of Separation Science 32:4048-4051 ( 2009).
Yamamoto, S. et al., (Abstracts of Papers, 239th ACS National Meeting, San Francisco, Mar. 21-25, 2010, BIOT-569 Publisher: American Chemical Society, Washington, D.C.).
Zhou et al., "PEG-Modulated Column Chromatography for Purification of Recombinant Adeno-Associated Virus Serotype 9" Journal of Virological Methods 173:99-107 ( 2011).
Feng et al., "Polyethylene glycol improves the purification of recombinant human tumor necrosis factor during ion exchange chromatography" Biotechnology Techniques 12(4):289-293 ( 1998).
Gagnon, "Improved antibody aggregate removal by hydroxyapatite chromatography in the presence of polyethylene glycol" J Immunol Methods 31(2):222-8 ( 2008).
Gagnon, "Method for obtaining unique selectivities in ion-exchange chromatography by addition of organic polymers to the mobile phase" Journal of Chromatography A 743:51-55 ( 1996).
Gagnon, Validated Biosystems:'Fine-Tuning Selectivity on Ion Exchangers', Dec. 31, 1999. Retrieved from the Internet:URL:http://www.validated.com/revalbio/pdffiles/ionselect.pdf.
Milby et al., "Ion-exchange chromatography of proteins: The effect of neutral polymers in the mobile phase" J. Chromatography 482(1):133-144 (Nov. 17, 1989).
PCT IPRP for PCT/EP2012/054449.

* cited by examiner

*Primary Examiner* — Daniel E Kolker
*Assistant Examiner* — James Roger

(57) ABSTRACT

Herein is reported a method for producing a polypeptide in monomeric form comprising the following step: recovering the polypeptide in monomeric form from an ion exchange chromatography material by applying a solution comprising a non-ionic polymer and an additive.

4 Claims, 6 Drawing Sheets

Figure 1:
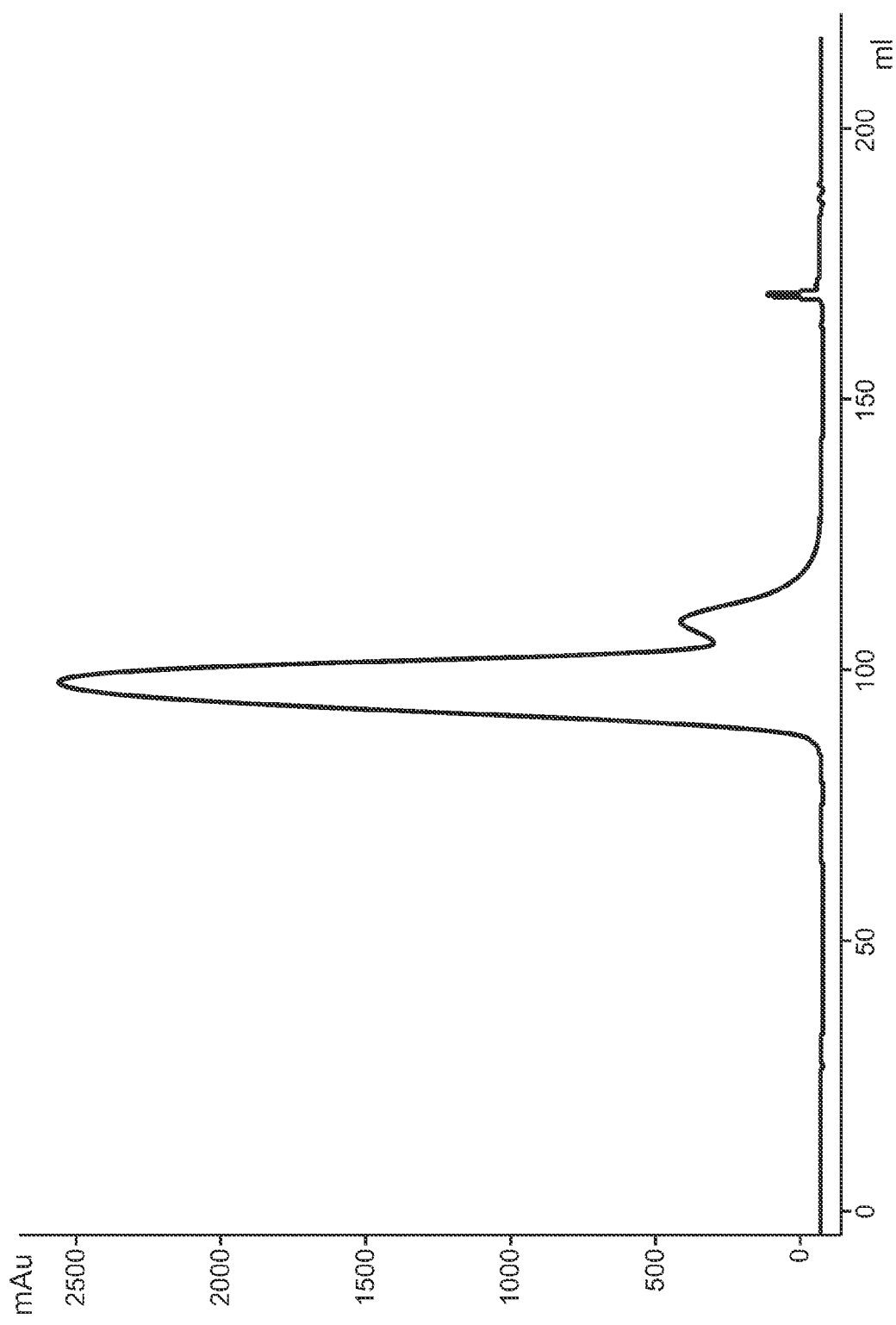

ION EXCHANGE CHROMATOGRAPHY WITH IMPROVED SELECTIVITY FOR THE SEPARATION OF POLYPEPTIDE MONOMERS, AGGREGATES AND FRAGMENTS BY MODULATION OF THE MOBILE PHASE

CROSS REFERENCE TO RELATED APPLICATIONS

This application is a continuation of International Application No. PCT/EP2012/054449 having an international filing date of Mar. 14, 2012, the entire contents of which are incorporated herein by reference, and which claims benefit under 35 U.S.C. §119 to European Patent Application No. 11158523.8 filed Mar. 16, 2011.

Herein is reported a method for separating polypeptide monomers, aggregates and fragments using ion exchange chromatography, whereby in the recovering step a non-ionic polymer and an additive are added to the mobile phase.

BACKGROUND OF THE INVENTION

Proteins and especially immunoglobulins play an important role in today's medical portfolio. Polypeptides for use in pharmaceutical applications are mainly produced in mammalian cells such as CHO cells, NS0 cells, Sp2/0 cells, COS cells, HEK cells, BHK cells, PER.C6® cells, and the like.

Due to their chemical and physical properties, such as molecular weight and domain architecture including secondary modifications, the downstream processing of immunoglobulins is very complicated. For example, are not only for formulated drugs but also for intermediates in downstream processing (DSP) concentrated solutions required to achieve low volumes for economic handling and application storage. The downstream processing of biotechnologically produced immunoglobulins typically comprises three chromatography steps: a first affinity chromatography step using e.g. Protein A, to remove non-immunoglobulin molecules, followed by two ion exchange chromatography steps. The purified immunoglobulin is obtained in a low concentration solution requiring a concentration step prior to formulating the antibody into the pharmaceutical formulation. Many proteins, including IgG, form dimers, oligomers or higher order aggregates. In order to provide a therapeutic protein product with the required purity these molecule species have to be removed by the purification process.

Different methods are well established and widely used for protein purification (Vijayalakshmi, M. A., Appl. Biochem. Biotech. 75 (1998) 93-102). Zhou, J. X., et al. (J. Chrom. A 1175 (2007) 69-80) report a pH-conductivity hybrid gradient cation-exchange chromatography for process-scale monoclonal antibody purification. The separation of antibody monomers from its multimers by use of ion exchange chromatography is reported in EP 1 084 136. U.S. Pat. No. 5,429, 746 relates to the application of hydrophobic interaction chromatography combination chromatography to the purification of antibody molecule proteins.

Solvent modulation of column chromatography is reported by Arakawa, T., et al. in Prot. Pep. Lett. 15 (2008) 544-555. In EP 1 729 867 a method for chromatographic purification is reported. Antibody aggregate removal by hydroxyapatite chromatography is reported by Gagnon, P. and Beam, K., in Curr. Pharm. Biotechnol. 10 (2009) 440-446. In J. Immunol. Meth. (336 (2008) 222-228) reports Gagnon, P., an improved antibody aggregate removal by hydroxyapatite chromatography in the presence of polyethylene glycol. In WO 2004/013162 an increased dynamic binding capacity in ion exchange chromatography by addition of polyethylene glycol is reported. In WO 2005/094960 a method for chromatographic purification is reported. Enhanced capacity and purification of antibodies by mixed mode chromatography in the presence of aqueous-soluble non-ionic organic polymers is reported in WO 2008/086335. In WO 2009/149067 a process for the purification of antibodies is reported.

Milby, K. H., et al. report the ion-exchange chromatography of proteins and the effect of neutral polymers in the mobile phase (J. Chrom. 482 (1989) 133-144). In Biotechnology Techniques (12 (1998) 289-293) Feng, X-L., et al. report that polyethylene glycol improves the purification of recombinant human tumor necrosis factor during ion exchange chromatography. A method for obtaining unique selectivities in ion-exchange chromatography by addition of organic polymers to the mobile phase is reported by Gagnon, P., et al. (J. Chrom. 743 (1996) 51-55). Gagnon, P., reports in an internet article on validated.com (http://www.validated-.com/revalbio/pdffiles/ionslect.pdf) the fine-tuning of selectivity on ion exchangers. In WO 2009/149067 a process for the purification of antibodies is reported.

SUMMARY OF THE INVENTION

It has been found that high PEG-concentrations can be employed during cation exchange chromatography in the presence of certain additives (solubility enhancers) in order to modulate selectivity and to improve resolution of antibody monomer and aggregate species, e.g. compared to methods employing PEG-only.

Herein is reported a method for isolating or obtaining or producing a polypeptide of interest in monomeric form from other component(s), such as the polypeptide of interest in aggregated form, comprising at least one chromatographic step. In one embodiment the method comprises contacting a solution comprising the polypeptide of interest with a cation-exchange chromatography material wherein the contacting with the chromatography material takes place in the absence of a non-ionic polymer and an additive, and wherein the recovering takes place in the presence of a non-ionic polymer and an additive.

It has been found that by using an additional additive in a method as reported herein the effect of the non-ionic polymer can be improved.

One aspect as reported herein is a method for producing an antibody in monomeric form comprising the following steps:
  applying a solution comprising a non-ionic polymer and an additive to a chromatography material to which an antibody had been adsorbed, whereby the antibody in monomeric form remains adsorbed to the ion exchange chromatography material, and
  recovering the antibody in monomeric form from the ion exchange chromatography material by applying a solution comprising a non-ionic polymer, an additive, and an elution compound, and thereby producing the antibody in monomeric form.

Another aspect as reported herein is a method for producing a polypeptide preparation with reduced host cell protein content whereby the preparation is obtained from a mammalian cell cultivation supernatant, especially a CHO cell cultivation supernatant, comprising the following steps:
  applying a solution comprising a non-ionic polymer and an additive to a chromatography material to which the polypeptide had been adsorbed, whereby the polypeptide in monomeric form remains adsorbed to the ion exchange chromatography material, and recovering the polypeptide in monomeric form from the ion exchange chromatography material by applying a solution comprising a non-ionic polymer, an additive, and an elution compound, and thereby producing the polypeptide preparation with reduced host cell protein content.

One aspect as reported herein is a method for determining the concentration of a non-ionic polymer and an additive for use in an ion exchange chromatography of a polypeptide comprising the following steps:

determining in solution in the absence of the additive the concentration of the non-ionic polymer at which less than 50% of the polypeptide remain in solution, determining in solution in the presence of a concentration of the non-ionic polymer, which has been determined in the previous step, the concentration of the additive at which more than 95% of the polypeptide remain in solution, thereby determining the concentration of a non-ionic polymer and an additive.

One aspect as reported herein is a method for producing an antibody in monomeric form comprising the following step:

recovering the antibody in monomeric form from an ion exchange chromatography material by applying a solution comprising a non-ionic polymer, an additive, and an elution compound, and thereby producing the antibody in monomeric form, wherein the separation efficiency (resolution) of the chromatography is enhanced compared to a chromatography in the absence of the non-ionic polymer, and wherein the employed concentration of the non-ionic polymer would result in a partial or complete precipitation of the antibody in the absence of the additive.

In one embodiment the ion exchange chromatography material is a cation exchange chromatography material.

In one embodiment the non-ionic polymer is selected from the group comprising poly (ethylene glycol) (PEG), poly (propylene glycol) (PPG), PEG-PPG copolymers, and tri-block copolymers composed of poly (oxypropylene) (poly (propylene oxide)) flanked by poly (oxyethylene) (poly (ethylene oxide)). In a further embodiment the non-ionic polymer is poly (ethylene glycol).

In one embodiment the additive is selected from the group comprising zwitterions, amino acids, urea, urea derivatives, ampholytes, CHAPSO, natural products, sugars, and polyols. In a further embodiment the additive is sorbitol.

In one embodiment the non-ionic polymer has a concentration of from about 5% to 15% by weight and/or the additive has a concentration of from 3% to 25% by weight.

In one embodiment the polypeptide is an antibody of class IgG, or IgD, or IgE, or IgA. In another embodiment the polypeptide is an antibody of class IgG, subclass IgG1, or subclass IgG2, or subclass IgG3, or subclass IgG4.

In one embodiment the method comprises the following steps:

applying a first solution that optionally comprises a non-ionic polymer and an additive to an ion exchange chromatographic material and thereby equilibrating the ion exchange chromatography material, applying a buffered solution comprising the polypeptide to the equilibrated chromatography material and thereby adsorbing the polypeptide to the chromatography material, whereby the solution is essentially free of a non-ionic polymer and an additive, applying a buffered solution comprising a non-ionic polymer and an additive to the chromatography material, whereby the polypeptide in monomeric form remains adsorbed to the ion exchange chromatography material, and recovering the polypeptide in monomeric form from the ion exchange chromatography material by applying a solution comprising a non-ionic polymer, an additive, and an elution compound.

In one embodiment the polypeptide is an antibody.

In one embodiment about 40 g polypeptide (antibody) are applied per liter of chromatography material. In one embodiment about 30 g polypeptide (antibody) are applied per liter of chromatography material. In one embodiment about 20 g polypeptide (antibody) are applied per liter of chromatography material.

DETAILED DESCRIPTION OF THE INVENTION

Herein is reported a method for producing a polypeptide of interest in monomeric form by separating it from other component(s), such as the polypeptide of interest in aggregated form, comprising at least one chromatographic step. In one embodiment the method comprises contacting a solution comprising the polypeptide of interest and a cation-exchange chromatography material wherein the contacting with the chromatography material takes place in the absence of a non-ionic polymer and an additive and wherein the recovering takes place in the presence of a non-ionic polymer and an additive.

It has been found that the presence of a non-ionic polymer and an additive increases the retention time difference (resolution) of a polypeptide in monomeric form compared to the polypeptide in aggregated form on a cation exchange chromatography material, thereby enabling novel selectivity for improved removal of a polypeptide in aggregated form from the polypeptide in monomeric form.

Especially it has been found that high PEG-concentrations can be employed during cation exchange chromatography in the presence of certain additives (solubility enhancers) in order to modulate selectivity and to improve resolution of antibody monomer and aggregate species, e.g. compared to methods employing PEG-only.

Poly (ethylene glycol) is viscous and high viscosities of the running buffers in chromatographic applications lead to certain practical limitations during chromatographic applications.

A chromatographic separation process can be characterized by the resolution of the individual peaks in the elution chromatogram. The resolution value can be calculated according to Kaltenbrunner, O., et al., Biotechnol. Bioeng. 98 (2007) 201-210, or Grushka, E., Anal. Chem. 44 (1972) 1733-1738.

General chromatographic methods and their use are known to a person skilled in the art. See for example, Heftmann, E., (ed.), Chromatography, 5$^{th}$ edition, Part A: Fundamentals and Techniques, Elsevier Science Publishing Company, New York, (1992); Deyl, Z., (ed.), Advanced Chromatographic and Electromigration Methods in Biosciences, Vol. 60, Elsevier Science BV, Amsterdam, The Netherlands, (1998); Poole, C. F., and Poole, S. K., Chromatography Today, Elsevier Science Publishing Company, New York (1991); Scopes, Protein Purification: Principles and Practice, Springer Verlag (1982); Sambrook, J. et al., (ed.), Molecular Cloning: A Laboratory Manual, Second Edition, Cold Spring Harbor Laboratory Press, Cold Spring Harbor, N.Y. (1989); or Ausubel, F. M. et al., (eds.), Current Protocols in Molecular Biology, John Wiley & Sons, Inc., New York (1998).

A "polypeptide" is a polymer of amino acid residues joined by peptide bonds, whether produced naturally or synthetically. Polypeptides of less than about 20 amino acid residues are referred to as "peptides". A "protein" is a macromolecule comprising one or more polypeptide chains or at least one polypeptide chain of more than 100 amino acid residues. A polypeptide may also comprise non-peptidic components, such as carbohydrate groups. Carbohydrate groups and other non-peptidic substituents may be added to a polypeptide by the cell in which the polypeptide is produced, and will vary with the type of cell. Polypeptides are defined herein in terms of their amino acid backbone structures; substituents such as carbohydrate groups are generally not specified, but may be present nonetheless.

The term "applying to" denotes a partial step of a purification method in which a solution is brought in contact with a chromatography material. This denotes that either a) the solution is added to a chromatographic device in which the chromatography material is contained, or b) that the chromatography material is added to a solution comprising the polypeptide. In case a) the solution passes through the device allowing for the adsorption of the substances contained in solution to the chromatography material. Depending on the conditions, such as e.g. pH, conductivity, salt concentration, temperature, and/or flow rate, some substances of the solution adsorb to the chromatography material and other substances can be recovered from the flow-through. The "flow-through" denotes the solution obtained after the passage of the device, which may either be the applied solution or a buffered solution, which is used to wash the column or to cause elution of substances adsorbed to the chromatography material. In one embodiment the device is a column or a cassette. In case b) the chromatography material can be added, e.g. as a solid, to the solution, e.g. containing the substance of interest to be purified, allowing for an interaction between the chromatography material and the substances in solution. After the interaction the chromatography material is removed, e.g. by filtration, and the substance bound to the chromatography material are also removed therewith from the solution whereas the substances not bound to the chromatography material remain in solution. In one embodiment about 40 g polypeptide (antibody) are adsorbed per liter of chromatography material. In one embodiment about 30 g polypeptide (antibody) are adsorbed per liter of chromatography material. In one embodiment about 20 g polypeptide (antibody) are adsorbed per liter of chromatography material.

The term "bind-and-elute mode" denotes an operation mode of a chromatography step, in which a solution containing a substance of interest to be purified is applied to a chromatography material, whereby the substance of interest binds to the chromatography material. Thus, the substance of interest is retained on the chromatography material whereas substances not of interest are removed with the flow-through or the supernatant. The substance of interest is afterwards recovered from the chromatography material in a second step with an elution solution. In one embodiment the method as reported herein is operated in bind-and-elute mode.

The solutions employed in the method as reported herein are crude or buffered solutions. The term "buffered solution" denotes a solution in which changes of pH due to the addition or release of acidic or alkaline substances is leveled by the dissolved buffer substance. Any buffer substance with such properties can be used. Generally pharmaceutically acceptable buffers substances are used. In one embodiment the buffered solution is selected from a phosphate buffered solution consisting of phosphoric acid and/or salts thereof, or an acetate buffered solution consisting of acetic acid and salts thereof, or a citrate buffered solution consisting of citric acid and/or salts thereof, or a morpholine buffered solution, or a 2-(N-morpholino) ethanesulfonic buffered solution, or a histidine buffered solution, or a glycine buffered solution, or a tris (hydroxymethyl) aminomethane (TRIS) buffered solution. In another embodiment the buffer solution is selected from a phosphate buffered solution, or an acetate buffered solution, or a citrate buffered solution, or a histidine buffered solution. Optionally the buffered solution may comprise an additional salt, such as e.g. sodium chloride, sodium sulphate, potassium chloride, potassium sulfate, sodium citrate, or potassium citrate.

The terms "continuous elution" and "continuous elution method" denote a method wherein the conductivity of a solution causing elution, i.e. the recovery of a bound compound from a chromatography material, is changed, i.e. raised or lowered, continuously, i.e. the concentration is changed by a sequence of small steps each not bigger than a change of 2%, or of 1% of the concentration of the substance causing elution. In this "continuous elution" one or more conditions, for example the pH, the ionic strength, concentration of a salt, and/or the flow of the mobile phase can be changed linearly or exponentially or asymptotically. In one embodiment the change is linear.

The term "step elution" denotes a method wherein e.g. the concentration of a substance causing elution, i.e. the recovery of a bound substance from a chromatography material, is raised or lowered at once, i.e. directly from one value/level to the next value/level. In this "step elution" one or more conditions, for example the pH, the ionic strength, concentration of a salt, and/or the flow of a chromatography, can be changed all at once from a first, e.g. starting, value to a second, e.g. final, value. Thus, the conditions are changed incrementally, i.e. stepwise, in contrast to a linear change.

The term "ion exchange chromatography material" denotes an immobile high molecular weight matrix that carries covalently bound charged substituents used as stationary phase in ion exchange chromatography. For overall charge neutrality not covalently bound counter ions are bound thereto. The "ion exchange chromatography material" has the ability to exchange its not covalently bound counter ions for similarly charged ions of the surrounding solution. Depending on the charge of its exchangeable counter ions the "ion exchange resin" is referred to as cation exchange resin or as anion exchange resin. Depending on the nature of the charged group (substituent) the "ion exchange resin" is referred to as, e.g. in the case of cation exchange resins, sulfonic acid resin (S), or sulfopropyl resin (SP), or carboxymethyl resin (CM).

Different types of ion exchange materials, i.e. stationary phases, are available under different names and from a multitude of companies such as e.g. cation exchange materials Bio-Rex® (e.g. type 70), Chelex® (e.g. type 100), Macro-Prep® (e.g. type CM, High S, 25 S), AGO (e.g. type 50W, MP) all available from BioRad Laboratories, WCX 2 available from Ciphergen, Dowex® MAC-3 available from Dow chemical company, Mustang C and Mustang S available from Pall Corporation, Cellulose CM (e.g. type 23, 52), hyper-D, partisphere available from Whatman plc., Amberlite® IRC (e.g. type 76, 747, 748), Amberlite® GT 73, Toyopearl® (e.g. type SP, CM, 650M) all available from Tosoh Bioscience GmbH, CM 1500 and CM 3000 available from BioChrom Labs, SP-Sepharose™, CM-Sepharose™ available from GE Healthcare, Poros resins available from Applied Biosystems or PerSeptive Biosystems, Asahipak ES (e.g. type 502C), CXpak P, IEC CM (e.g. type 825, 2825, 5025, LG), IEC SP (e.g. type 420N, 825), IEC QA (e.g. type LG, 825) available from Shoko America Inc., 50W cation exchange resin available from Eichrom Technologies Inc. In one embodiment the cation exchange material is a strong cation exchange material such as Macro-Prep® High 5 or 255, or MacroCap SP, or Toyopearl® SP 650M, or Source S, or SP Sepharose, or POLYCAT A, or Mono S, or Highscreen SP.

The term "under conditions suitable for binding" and grammatical equivalents thereof denotes that a substance of interest, e.g. an antibody in monomeric form, binds to a stationary phase when brought in contact with it, e.g. an ion exchange material. This does not necessarily denote that 100% of the substance of interest is bound but essentially 100% of the substance of interest is bound, i.e. at least 50% of the substance of interest is bound, in one embodiment at least 75% of the substance of interest is bound, in another embodiment at least 85% of the substance of interest is bound, in a further embodiment more than 95% of the substance of interest is bound to the stationary phase.

In one embodiment the antibody is a therapeutic antibody. The term "therapeutic antibody" denotes an antibody which is tested in clinical studies for approval as human therapeutic and which can be administered to an individual for the treatment of a disease. In another embodiment the therapeutic antibody is a monoclonal antibody. In a further embodiment the therapeutic antibody is obtained from a great ape or an animal transformed with a human antibody locus or a human monoclonal antibody or a humanized monoclonal antibody. In one embodiment the therapeutic antibody is a human monoclonal antibody. In a further embodiment the therapeutic antibody is a humanized monoclonal antibody. Therapeutic antibodies are being used widely for the treatment of various diseases such as oncological diseases (e.g. hematological and solid malignancies including non-Hodgkin's lymphoma, breast cancer, and colorectal cancer), immunological diseases, central nervous diseases, vascular diseases, or infectious diseases. Such antibodies are, in one embodiment antibodies against ALK, adhesion related kinase receptor (e.g., Ax1), or ERBB receptors (e.g., EGFR, ERBB2, ERBB3, ERBB4), or erythropoietin-producing hepatocellular (EPH) receptors (e.g., EphA1; EphA2, EphA3, EphA4, EphA5, EphA6, EphA7, EphA8, EphB1, EphB2, EphB3, EphB4, EphB5, EphB6), or fibroblast growth factor (FGF) receptors (e.g., FGFR1, FGFR2, FGFR3, FGFR4, FGFR5), or Fgr, or IGF-1R, or Insulin Receptor, or LTK, or M-CSFR, or MUSK, or platelet-derived growth factor (PDGF) receptors (e.g., PDGFR-A, PDGFR-B), or RET, or ROR1, or ROR2, or ROS, or RYK, or vascular endothelial growth factor (VEGF) receptors (e.g., VEGF-R1/FLT1, VEGF-R2/FLK1, VEGF3), or tyrosine kinase with immunoglobulin-like and EGF-like domains (TIE) receptors (e.g., TIE-1, TIE-2/TEK), or Tec, or TYRO10, or insulin-like growth factor (IGF) receptors (e.g., INS-R, IGF-IR, IR-R), or Discoidin Domain (DD) receptors (e.g., DDR1, DDR2), or receptor for c-Met (MET), or recepteur d'origine nantais (RON, also known as macrophage stimulating 1 receptor), or FLT3 (fms-related tyrosine kinase 3), or colony stimulating factor 1 (CSF1) receptor, or receptor for c-kit (KIT, or SCF-R), or insulin receptor related (IRR) receptors, or CD19, or CD20, or HLA-DR, or CD33, or CD52, or G250, or GD3, or PSMA, or CD56, or CEA, or Lewis Y antigen, or IL-6 receptor.

The term "antibody" encompasses the various forms of antibody structures including whole antibodies. The antibody is in one embodiment a human antibody, a humanized antibody, a chimeric antibody, or a T cell antigen depleted antibody. Genetic engineering of antibodies is e.g. described in Morrison, S. L., et al., Proc. Natl. Acad. Sci. USA 81 (1984) 6851-6855; U.S. Pat. No. 5,202,238; U.S. Pat. No. 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125. Depending on the amino acid sequence of the constant region of the heavy chains, antibodies are divided in the classes: IgA, IgD, IgE, and IgG. Some of these classes are further divided into subclasses (isotypes), i.e. IgG in IgG1, IgG2, IgG3, and IgG4, or IgA in IgA1 and IgA2. According to the class to which an antibody belongs are the heavy chain constant regions of antibodies denoted as $\alpha$ (IgA), $\delta$ (IgD), $\epsilon$ (IgE), and $\gamma$ (IgG), respectively. The term "antibody of human IgG1 class" for example denotes an antibody in which the amino acid sequence of the constant domains is derived from the amino acid sequence of human IgG1. The term includes human antibodies, humanized antibodies, chimeric antibodies, and antibody conjugates.

The term "complete antibody" denotes an antibody which comprises two light chain polypeptides (light chains) and two heavy chain polypeptides (heavy chains). Each of the heavy and light chain polypeptides contains a variable domain (variable region, generally the amino terminal portion) comprising binding regions that are able to interact with an antigen. Each of the heavy and light chain polypeptides comprises a constant region (generally the carboxyl terminal portion). The variable domain of a light or heavy chain in turn comprises different segments, i.e. four framework regions (FR) and three hypervariable regions (CDR).

The term "antibody conjugate" denotes a polypeptide comprising at least one domain of an antibody heavy or light chain conjugated via a peptide bond to a further polypeptide. The further polypeptide can be a non-antibody peptide, such as a hormone, or toxin, or growth receptor, or antifusogenic peptide, or complement factor, or the like.

For the purification of recombinantly produced antibodies a combination of different column chromatography steps can be employed. Generally a protein A affinity chromatography is followed by one or two additional separation steps. The final purification step is a so called "polishing step" for the removal of trace impurities and contaminants like aggregated antibodies, residual HCP (host cell protein), DNA (host cell nucleic acid), viruses, or endotoxins.

The term "antibody in monomeric form" denotes an antibody molecule that is not associated with a second antibody molecule, i.e. which is neither covalently nor non-covalently bound to another antibody molecule. The term "antibody in aggregated form" denotes an antibody molecule which is associated, either covalently or non-covalently, with at least one additional antibody molecule, and which is eluted in a single peak from a size exclusion chromatography column. The term "in monomeric form" as used herein not necessarily denotes that 100% of an antibody molecule is present in monomeric form. It denotes that an antibody is essentially in monomeric form, i.e. at least 90% of the antibody is in monomeric from, in one embodiment at least 95% of the antibody is in monomeric form, in another embodiment at least 99% of the antibody is in monomeric form, in a further embodiment at least 99.5% of the antibody is in monomeric form, and in also an embodiment more than 99.8% of the antibody is in monomeric form determined as peak area of a size exclusion chromatogram. The term "high molecular weight (HMW) form" denotes polymeric, i.e. aggregated, antibody, whereby this aggregate is still soluble in an aqueous buffered solution.

The term "100%" as used herein denotes that the amount of components other than a specified component is below the detection limit of the referred to analytical method under the specified conditions.

The terms "90%", "95%", "99%", "99.5%", and "99.8%" as used within this application denote no exact values but values within the accuracy of the referred to analytical method under the specified conditions.

The term "elution compound" denotes a salt used for recovering of a bound polypeptide from an ion exchange material, whereby the compound increases the conductivity of the buffer/solution. This can be accomplished either by an increased buffer salt concentration or by the addition of other salts, so called elution salts, to the buffered solution. Preferred elution salts are sodium citrate, sodium chloride, sodium sulphate, sodium phosphate, potassium chloride, potassium sulfate, potassium phosphate, as well as other salts of citric and phosphoric acid, and any mixture of these components. In one embodiment the elution compound is selected from sodium citrate, sodium chloride, potassium chloride, and mixtures thereof.

"Humanized" forms of non-human (e.g. rodent) antibodies are chimeric antibodies that contain partial sequences derived from a non-human antibody and from a human antibody. For the most part, humanized antibodies are derived from a human antibody (recipient antibody), in which residues from a hypervariable region are replaced by residues from a hypervariable region of a non-human species (donor antibody), such as mouse, rat, rabbit, sheep, guinea pig, or non-human primate, having the desired specificity and affinity. In some instances, framework region (FR) residues of the human antibody are replaced by corresponding non-human residues. Furthermore, humanized antibodies may comprise further modifications, e.g. amino acid residues that are not found in the recipient antibody or in the donor antibody. Such modifications result in variants of such recipient or donor antibody, which are homologous but not identical to the corresponding parent sequence. These modifications can be made to further refine antibody performance.

In general, a humanized antibody will comprise substantially all of at least one, and typically two, variable domains, in which all or substantially all of the hypervariable loops correspond to those of a non-human donor antibody and all or substantially all of the FRs are those of a human recipient antibody. The humanized antibody optionally will also comprise at least a portion of an antibody constant region, typically that of a human antibody.

In practice, humanized antibodies are typically human antibodies in which some hypervariable region residues and possibly some framework region residues are substituted by residues from analogous sites in rodent or non-human primate antibodies.

The term "monoclonal antibody" as used herein refers to an antibody obtained from a population of substantially homogeneous antibodies, i.e. the individual antibodies of the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different antigenic sites (determinants or epitopes), each monoclonal antibody is directed against a single antigenic site on an antigen. In addition to their specificity, monoclonal antibodies are advantageous in that they may be synthesized uncontaminated by other antibodies. The modifier "monoclonal" indicates the character of the antibody as being obtained from a substantially homogeneous population of antibodies and is not to be construed as requiring production of the antibody by any particular method.

The term "chimeric antibody" denotes an antibody comprising a variable domain, i.e. binding region, from a first species and at least a portion of a constant region derived from a different second species.

Amino acid sequence variants of antibodies can be prepared by introducing appropriate modifications into the nucleotide sequence encoding the antibody chains, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the antigen binding properties as the parent antibody.

Conservative amino acid substitutions are shown in Table 1 under the heading of "preferred substitutions". More substantial changes are provided in Table 1 under the heading of "exemplary substitutions", and as described below in reference to amino acid side chain classes. Amino acid substitutions may be introduced into the antibody chains and the products screened for retention of the biological activity of the parent antibody.

TABLE

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "mobile phase" denotes any mixtures of water and/or aqueous buffer and/or organic solvents being suitable to recover polypeptides from a chromatography column. The term "to elute" or "eluting", respectively, in the present context is used as known to the expert skilled in the art and denotes the dissolution, optionally the displacement, of adsorbed substance(s) from solids or adsorbents, which are impregnated with fluids, i.e., the column material to which the substance(s) is/are adsorbed.

The term "adsorption" denotes the accumulation of substances from a liquid, e.g. a mobile phase, at the boundary phase formed between the liquid and a solid phase, wherein the latter is able to adsorb the substances of interest at its surface. This adsorption leads to an accumulation of the adsorbed substances. The substance that is able to accumulate the substance of interest at its surface is referred to as adsorbent and the adsorbed material as adsorbate. The term adsorption is usually distinguished from the term "absorption" which beyond the accumulation at a surface also refers to the penetration of the accumulated substances into the interior of the adsorbing solid or fluid. In general, adsorption is a physical process in which substances usually molecules adhere to a surface of the adsorbent and thus, are accumulated at the respective surface. The forces being responsible for this adherence are considered to be physical forces rather than chemical bonds and thus, adsorption is also known in the art as physical adsorption or physisorption, which does not necessarily exclude chemical bonding of substances to the surface. The physical forces involved in the adsorption of substances to a surface are in most cases van der Waals-forces, London forces or dipole/dipole interactions, for example hydrogen bonds, or dipole-induced dipole interactions, wherein these terms are used as either explained herein or as normally used in context with adsorption.

In (column) chromatography usually solvents are used as eluent, i.e., eluting agent in which the substance(s) which are to be eluted are at least sufficiently soluble.

In one embodiment the non-ionic polymer is a hydrophilic non-ionic polymer. In a further embodiment the non-ionic polymer is selected from non-ionic polyether, such as poly (ethylene glycol), poly (propylene glycol) (PPG), PEG-PPG block copolymers, PEG-PPG copolymers, triblock copolymers composed of poly (oxypropylene) (poly (propylene oxide)) and two poly (oxyethylene) (poly (ethylene oxide)) polymers (Poloxamer, Pluronic™), and other PEG-PPG-PEG triblock polymers.

The employed non-ionic polymer can be characterized besides its monomeric building block by its molecular weight given in Daltons (Da). The term "molecular weight" denotes with respect to polymers the mean molecular weight of the polymer because polymeric compounds are not obtained with a defined molecular weight but in fact they have a molecular weight distribution. The molecular weight of a polymer is given in the form "about X Da", whereby "X" denotes the mean value of the molecular weight of the polymer. The term "about" indicates that in the polymer preparation, some molecules will have a weight more and some molecules will have a weight less than the indicated mean molecular weight, i.e. the term about refers to a molecular weight distribution in which 95% of the polymer molecules have a molecular weight within +/−30% of the indicated molecular weight. For example, a molecular weight of 3,500 Da denotes a range of from 2450 kDa to 4,550 Da. In one embodiment the polymer molecules have a molecular weight within +/−20% of the indicated molecular weight. In one embodiment the polymer molecules have a molecular weight within +/−10% of the indicated molecular weight.

The non-ionic polymer can be present in a buffered solution, such as a salt containing buffered solution. The solution comprising the polypeptide of interest can be obtained directly from the cultivation supernatant of a cell which comprises a nucleic acid encoding the polypeptide. The supernatant can be a clarified or a non-clarified cultivation supernatant.

In one embodiment one or more non-ionic polymers are present in the solution applied to the chromatography material for recovering the polypeptide, especially the antibody. In one embodiment the solution applied to the chromatography material for recovering the antibody in monomeric from comprises one, or two, or three, or four, or five different non-ionic polymers. If more than one non-ionic polymer is present in the solution the sum of the concentrations of all non-ionic polymers present in the solution is preferably within the range as given herein.

In one embodiment one or more additives are present in the solution applied to the chromatography material for recovering the polypeptide, especially the antibody. In one embodiment the solution applied to the chromatography material for recovering the antibody in monomeric from comprises one, or two, or three, or four, or five different additives. If more than one additive is present in the solution the sum of the concentrations of all additives present in the solution is preferably within the range as given herein.

Alternatively, the solution comprising the polypeptide of interest can be the eluate from a preceding chromatography step.

The interactions between the polypeptide of interest and the ion exchange chromatography material can be adsorption, i.e. binding of the polypeptide, or a retardation of the polypeptide in relation to other component(s) also present in the solution.

In order to recover a polypeptide in monomeric form from the ion exchange chromatography material the adsorption is followed by a step of eluting the adsorbed polypeptide of interest in monomeric form from the ion exchange chromatography material. Elution of adsorbed polypeptide can be effected by change of salt conditions, i.e. conductivity, and/or the pH value as compared to the adsorption step.

With the exception of the addition of a non-ionic polymer and an additive to the mobile phases during the recovering or eluting of the polypeptide of interest from the ion exchange chromatography material, the chromatography steps of the method as reported herein are performed in accordance with conventional general operating conditions and well known principles in the field. Conventional chromatography columns are conveniently used, the size of which are adapted for each case, as is the starting materials, buffers, matrices, including the functional groups of the ligands, etc.

The charge of a polypeptide may be changed by changing the pH value of the surrounding solution. It is well known, that an ion exchange material may be a strong ion exchange material, which means that it is charged at all pH values, or a weak ion exchange material, which means that it is chargeable by shifting the pH.

Adding a non-ionic polymer and an additive to the mobile phase in an ion exchange chromatography recovering step as reported herein was unexpectedly shown to increase the yield of the polypeptide in monomeric form, as compared to conventional ion exchange chromatography. In one embodiment the ion exchange chromatography is a cation exchange chromatography. In one embodiment the concentration of the non-ionic polymer is at least about 5% by weight and the concentration of the additive is at least 3% by weight.

There are in general no molecular weight exclusions for the non-ionic polymer used in the method as reported herein. The molecular weight of the non-ionic polymer is chosen in a way that is as low as possible while resulting in combination with the additive in an increased yield of the polypeptide in monomeric form compared to the used of the non-ionic polymer alone. The person skilled in the art knows that the addition of any substance, i.e. of the non-ionic polymer and the additive, affects (increases) the viscosity of the resulting solution. Therefore a person skilled in the art will appreciate that due to the physicochemical properties of the non-ionic polymer and the additive an upper limit for the addition of these compounds exists.

The non-ionic polymer used as in the method as reported herein comprises groups that are rich in oxygen atoms. In one embodiment the non-ionic polymer is an aqueous-soluble not-charged linear or branched polymer. Such non-ionic polymers are in one embodiment polyether, such as poly (ethylene glycol) (PEG), poly (propylene glycol) (PPG), PEG-PPG block copolymers, PEG-PPG copolymers, triblock copolymers composed of a central hydrophobic chain of poly (oxypropylene) (poly(propylene oxide)) flanked by two hydrophilic chains of poly (oxyethylene) (poly(ethylene oxide)) (Poloxamer, Pluronic™), and other PEG-PPG-PEG triblock polymers, ethylhydroxyethylcellulose (EHEC) and similar polymers, polymerized allylglycidyl ether, polymerized phenyl glycidyl ether, dextran, starch, cellulose, poly vinylpyrrolidone and various surfactants and other compounds comprising these building blocks. In one embodiment the non-ionic polymer is poly (ethylene glycol) (PEG). The term poly (ethylene glycol) also comprises poly (ethylene glycol)s which have been modified.

Any molecular weight non-ionic polymer can be used in the method as reported herein. However, the optimal concentration and ratio of the non-ionic polymer and the additive may vary for every protein and, in most cases, there is a preferable molecular weight of the non-ionic polymer and a preferable ratio of the non-ionic polymer to the additive.

In one embodiment the non-ionic polymer is poly (ethylene glycol).

Poly (ethylene glycol) can be used as a general model non-ionic polypeptide for behavior of non-ionic polymers within the method as reported herein. Thus, while poly (ethylene glycol) is used as an example herein it should be kept in mind that the provided information also applies to other non-ionic polymers, including to those specifically listed herein above.

Poly (ethylene glycol) is available from a number of commercial sources. In one embodiment the poly (ethylene glycol) has a molecular weight in the range of from about 100 Da to about 40,000 Da. In one embodiment the poly (ethylene glycol) has a molecular weight between about 400 Da and about 10,000 Da. In one embodiment the poly (ethylene glycol) has a molecular weight between about 1,000 Da and about 8,000 Da. In other embodiments, a mixture of different sized poly (ethylene glycol)s is utilized.

In one embodiment the poly (ethylene glycol) has a molecular weight between about 2,450 Da and about 4,550 Da. In one embodiment the poly (ethylene glycol) has a molecular weight between about 2,625 Da and about 4,375 Da. In one embodiment the poly (ethylene glycol) has a molecular weight between about 2,800 Da and about 4,200 Da. In one embodiment the poly (ethylene glycol) has a molecular weight between about 3,150 Da and about 3,850 Da.

In one embodiment the poly (ethylene glycol) is a linear or branched poly (ethylene glycol).

Lower molecular weight poly (ethylene glycols) can require a higher mass concentration to be used in order to have a similar effect compared to higher molecular weight poly (ethylene glycol)s.

Likewise lower concentrations of a poly (ethylene glycol) of a specified molecular weight can be employed to produce larger polypeptide in monomeric form, such as antibodies and fusion proteins, compared to those concentrations required to effect the same purity of smaller polypeptides. For example, an antibody of the class IgA, which is mostly present as a dimer, having a molecular weight of about 320 kDa will require a lower concentration of poly (ethylene glycol) compared to an antibody of the class IgG having a molecular weight of about 150 kDa. The retention of aggregates, complexes, and other large molecules can generally be increased more compared to that of the monomeric polypeptide. Also can a lower concentration of poly (ethylene glycol) be required to increase the retention of polypeptides that interact/are adsorbed strongly to the cation exchange chromatography material compared to the required concentration of poly (ethylene glycol) required to increase the adsorption of polypeptides that are normally adsorbed weakly to the cation exchange chromatography material.

The additive is a substance that can reduce or even prevent precipitation that is induced by the presence of the non-ionic polymer.

In one embodiment the additive has a conductivity that is sufficiently low to not interfere with a cation exchange chromatography. In another embodiment the additive has no detectable buffering capacity.

In one embodiment the additive is a zwitterion, or an amino acid (such as glycine, bicine, tricine, alanine, proline, Betaine), or urea, or an urea derivative (such as alkyl ureas (methyl urea, ethyl urea, etc.)), or alkylene glycols (such as ethylene glycol or propylene glycol), or an ampholyte (such as amino-sulfonic acid based buffers MES, MOPS, HEPES, PIPES and CAPS buffer), or CHAPSO, or a natural product (such as certain alkaloids and Betaines), or a sugar (such as glucose, sucrose, raffinose), or a polyol (such as glycerol, or xylitol, or sorbitol).

In one embodiment the additive is a zwitterion.

In one embodiment the additive is an amino acid. In a further embodiment the amino acid is glycine, or bicine, or tricine, or alanine, or proline, or Betaine.

In one embodiment the additive is urea or a urea derivative. In a further embodiment the additive is methyl urea or ethyl urea.

In one embodiment the additive is an alkylene glycol. In a further embodiment the alkylene glycol is ethylene glycol or propylene glycol.

In one embodiment the additive is an ampholyte. In a further embodiment the ampholyte is MES, or MOPS, or HEPES, or PIPES, or CAPS.

In one embodiment the additive is a natural product. In a further embodiment the natural product is an alkaloid or a Betaine.

In one embodiment the additive is a sugar. In a further embodiment the sugar is glucose, or sucrose, or raffinose, or fructose.

In one embodiment the additive is a polyol. In a further embodiment the polyol is glycerol, or xylitol, or sorbitol.

For any additive it has to be kept in mind that the individual solubility limit has to be considered when determining the respective amount or concentration employed.

If an amino acid is employed as additive it has to be kept in mind that a charged side chain will require the use of additional acid or base in order to adjust the pH value of the solution. By the addition of surplus acid or base the ionic strength of the mobile phase is change which in turn might have an influence on the chromatography result.

For example, glycine can be used as additive in the method as reported herein. Glycine is a zwitterionic compound, more precisely glycine is an amino acid. At pH values generally employed in cation exchange chromatography methods glycine does not contributes to overall conductivity and, thus, should not interfere in the cation exchange chromatography method. Additionally, glycine does not exhibit a buffering effect in aqueous solution it will also not effect the pH value of the mobile phase. Glycine can be used as additive in the method as reported herein in a concentration of from about 50 mM to 5 M. In one embodiment glycine has a concentration of from about 100 mM to about 4 M. In another embodiment glycine has a concentration of from about 250 mM to about 3 M. In a further embodiment glycine has a concentration of from about 500 mM to about 2 M. In still another embodiment glycine has a concentration of about 1 M. If more than one additive is used the concentrations of the individual additives can be lower than those exemplarily given in the paragraph above.

It has to be pointed out that any additive can be used at a concentration that is higher than the concentration necessary to achieve the intended effect. Especially a person skilled in the art can determine the additive concentration range in that the effect is present and that can be tolerated in the method as reported herein.

In one embodiment when the additive is urea or a urea derivative the additive is present in a concentration up to 6 molar. In one embodiment the additive is present in a concentration below 2 molar.

As outlined above the concentration of the non-ionic polymer and the additive in the recovering solution can vary. Generally, any concentration of poly (ethylene glycol) can be used. In one embodiment concentration of poly (ethylene glycol) is at least about 0.5% by weight. In one embodiment the concentration of poly (ethylene glycol) is at least about 0.5% by weight and at most about 20% by weight. In a further embodiment the concentration of poly (ethylene glycol) is at least about 5% by weight and at most about 15% by weight. In another embodiment the concentration of poly (ethylene glycol) is at least about 7% by weight and at most about 13% by weight.

The concentration of the non-ionic polymer can be held constant or it can be changed during the course of the chromatography. This change includes but is not limited to a gradient of increasing or decreasing concentration, or with step-wise changes in concentration.

In one embodiment the non-ionic polymer has a concentration of from about 0.5% to 20% by weight and/or the additive has a concentration of from 0.5% to 40% by weight.

In one embodiment the non-ionic polymer has a concentration of from about 5% to 15% by weight and/or the additive has a concentration of from 0.5% to 40% by weight.

In one embodiment the non-ionic polymer has a concentration of from about 5% to 15% by weight and/or the additive has a concentration of from 3% to 25% by weight.

In one embodiment the non-ionic polymer has a concentration of from about 7% to 13% by weight and/or the additive has a concentration of from 3% to 25% by weight.

In one embodiment the non-ionic polymer has a concentration of from about 7% to 13% by weight and/or the additive has a concentration of from 12% to 25% by weight.

In one embodiment the non-ionic polymer has a concentration of from about 7% to 13% by weight and/or the additive has a concentration of from 12% to 20% by weight.

The use or addition of a non-ionic polymer results in a reduction of the solubility of a polypeptide, especially of an antibody, concomitantly present in this solution. In the following Table the dependency of the solubility of an anti-IL17 antibody (5 mg/ml) as an exemplary polypeptide at room temperature (RT) and at 4° C. on the concentration of added poly (ethylene glycol) 3,500 Da is shown (50 mM sodium malonate, 90 mM NaCl, pH 6.5).

TABLE

| PEG-concentration | RT: protein conc. (UV280) [mg/ml] | RT: protein conc. [fraction of initial conc.] | 4° C.: protein conc. (UV280) [mg/ml] | 4° C.: protein conc. [fraction of initial conc.] |
|---|---|---|---|---|
| 0% | 5.0 | 100% | 5.1 | 100% |
| 1% | 5.1 | 100% | 5.1 | 100% |
| 2.5% | 5.1 | 100% | 5.1 | 100% |
| 5.0% | 5.1 | 100% | 5.8 | 100% |
| 7.5% | 5.0 | 100% | 2.1 | 42% |
| 10% | 2.5 | 50% | 0.5 | 10% |

In the following Table the dependency of the solubility of an anti-IL17 antibody (5 mg/ml) as an exemplary polypeptide at room temperature and at 4° C. on the concentration of added sodium chloride is shown (50 mM sodium malonate, 7.5 wt-% poly(ethylene glycol) with MW of 3,500 Da, pH 6.5).

TABLE

| NaCl-concentration | RT: protein conc. (UV280) [mg/ml] | RT: protein conc. [fraction of initial conc.] | 4° C.: protein conc. (UV280) [mg/ml] | 4° C.: protein conc. [fraction of initial conc.] |
|---|---|---|---|---|
| 0 mM | 2.9 | 61% | 0.7 | 14% |
| 45 mM | 3.3 | 67% | 0.8 | 17% |
| 90 mM | 3.6 | 75% | 0.9 | 19% |
| 135 mM | 4.0 | 83% | 1.0 | 20% |
| 180 mM | 4.6 | 95% | 1.6 | 33% |

Figure 3:
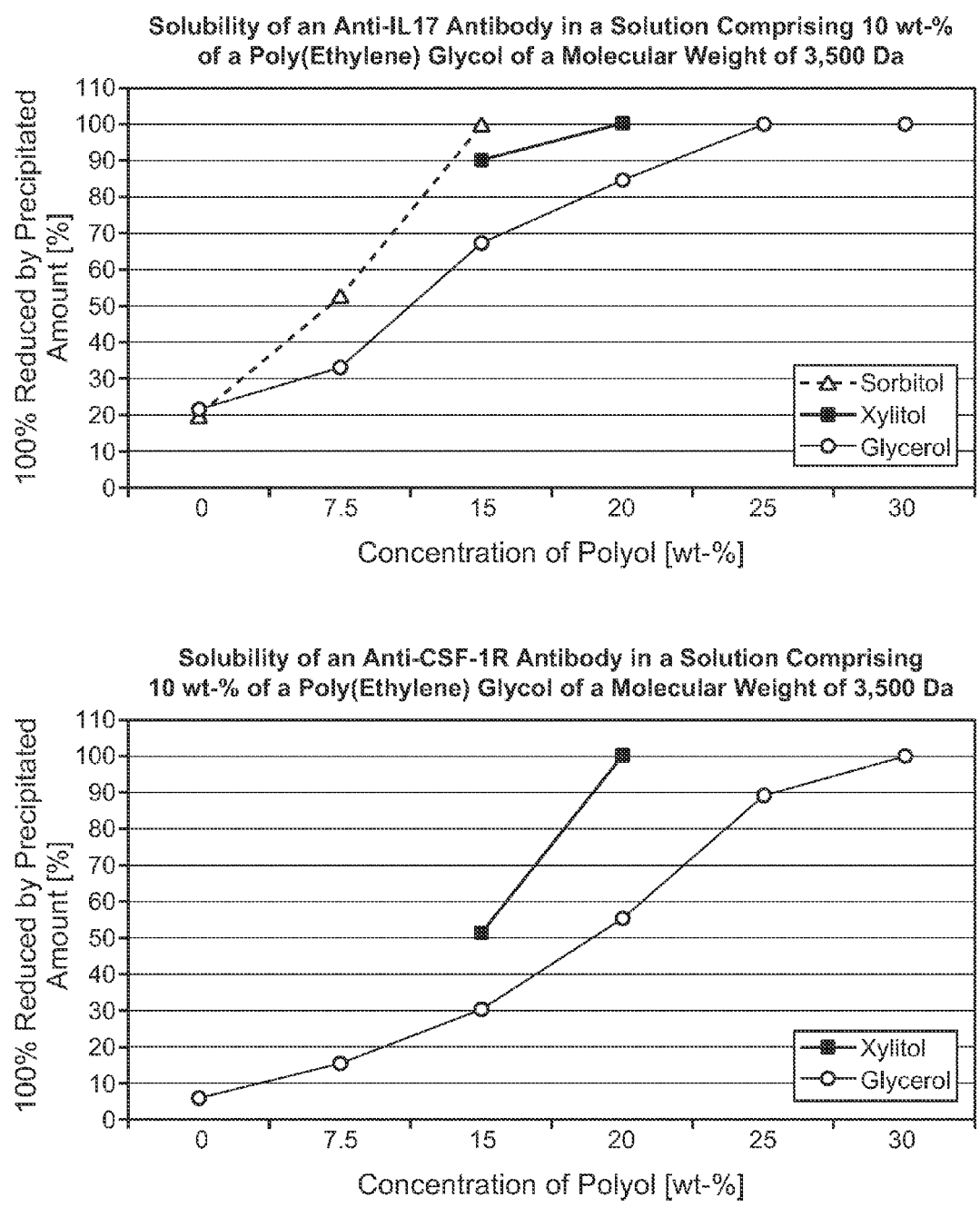

In one embodiment the non-ionic polymer is poly (ethylene glycol) and the additive is a polyol. In FIG. 3 the solubility of an antibody in a solution comprising poly (ethylene glycol) of a molecular weight of about 3,500 Da at a concentration of 10% by weight as an example of a non-ionic polymer and different polyols at varying concentration as additive are shown.

Figure 4:
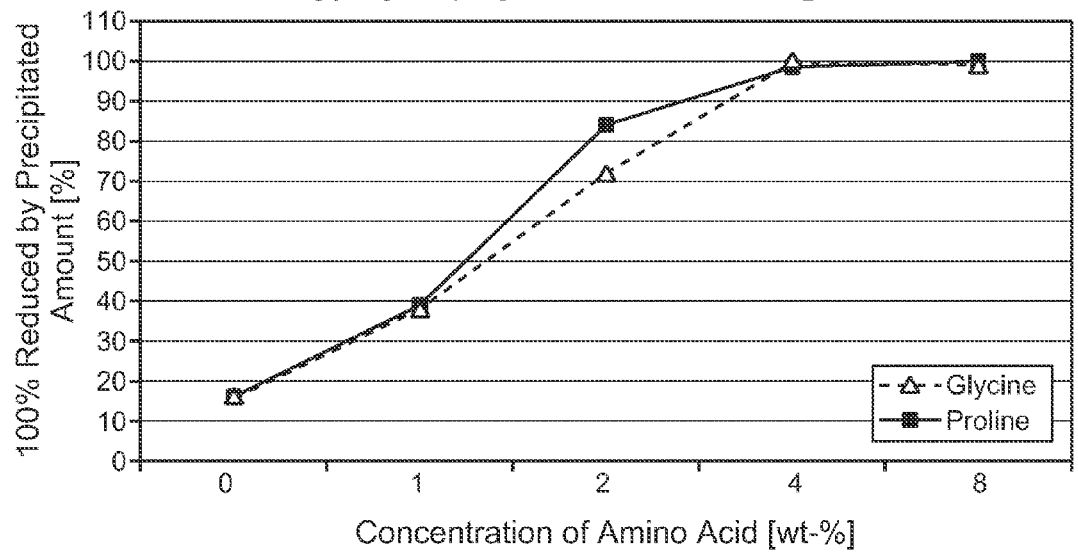
Figure 4:
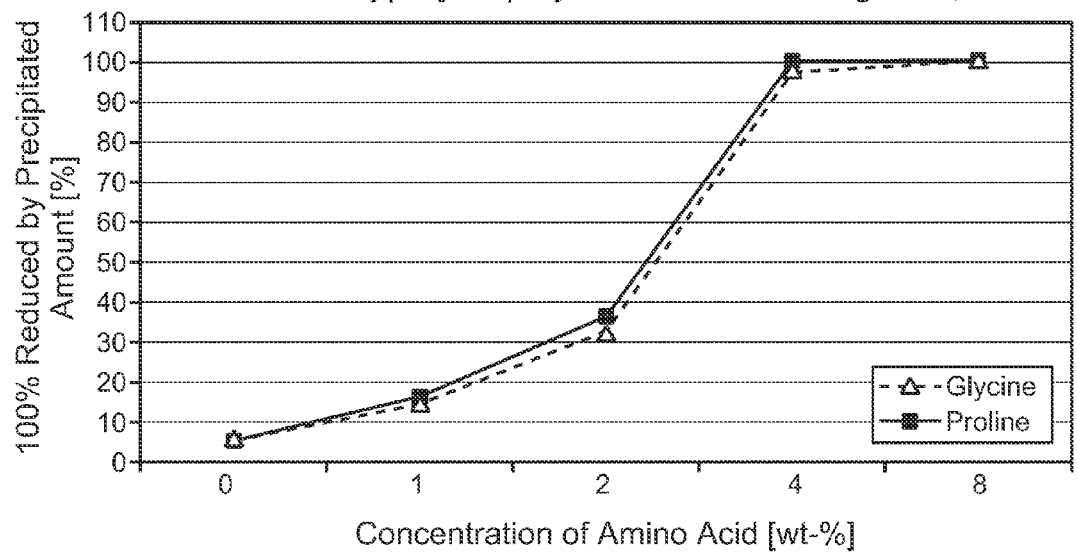

In one embodiment the non-ionic polymer is poly (ethylene glycol) with a molecular weight of about 3,500 Da and the additive is an amino acid. In FIG. 4 the solubility of an antibody in a solution comprising poly (ethylene glycol) with a molecular weight of about 3,500 Da at a concentration of 10% by weight as an example of a non-ionic polymer and different amino acids at varying concentration as additive is shown.

Figure 5:
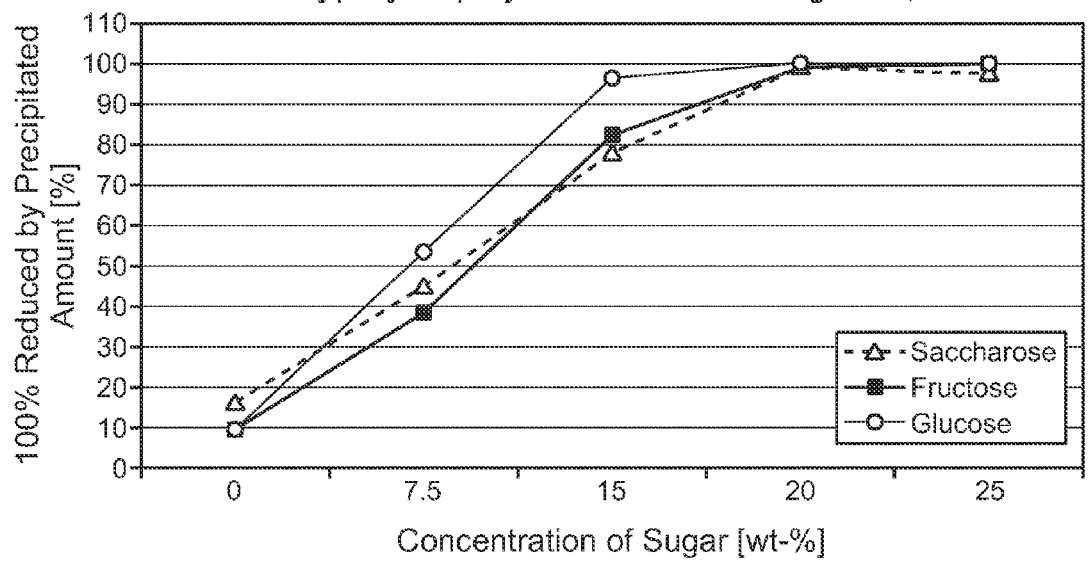
Figure 5:
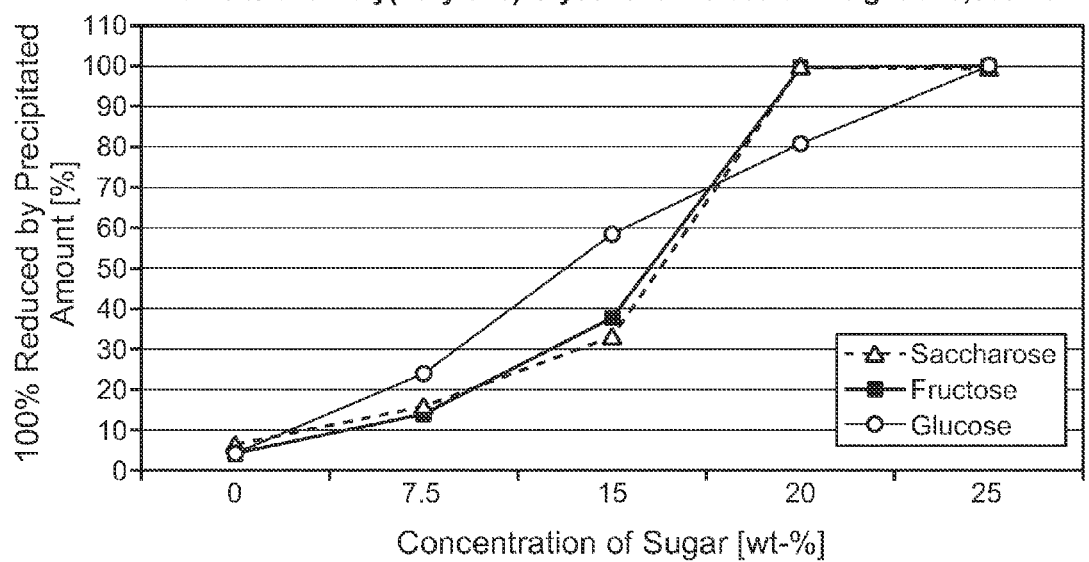

In one embodiment the non-ionic polymer is poly (ethylene glycol) with a molecular weight of about 3,500 Da and the additive is a sugar. In FIG. 5 the solubility of an antibody in a solution comprising poly (ethylene glycol) with a molecular weight of about 3,500 Da at a concentration of 10% by weight as an example of a non-ionic polymer and different sugars at varying concentration as additive is shown.

As can be seen from the following Table separations in the presence of only the additive do not provided for an improvement in the resolution value.

TABLE

| resolution value | anti-IL17 antibody | anti-CSF-1R antibody |
|---|---|---|
| None | 0.46 | 0.64 |
| Glycine | 0.52 | 0.61 |
| Glutamate | 0.49 | 0.68 |

TABLE-continued

| resolution value | anti-IL17 antibody | anti-CSF-1R antibody |
|---|---|---|
| Arginine | 0.53 | 0.73 |
| Glycerin | 0.49 | 0.68 |
| Urea | 0.46 | 0.66 |
| Mannitol | 0.46 | 0.69 |
| Sucrose | 0.46 | 0.39 |
| Trehalose | 0.45 | 0.60 |

In one embodiment the term "polyol" denotes a compound that has at least three hydroxyl groups, i.e. is a triol. Thus in one embodiment a polyol is selected from a triol that has three free hydroxyl groups, or a tetrol that has four free hydroxyl groups, or a pentaol that has five free hydroxyl groups, or a hexaol that has six free hydroxyl groups, or a heptaol that has seven free hydroxyl groups, or an octaol that has eight free hydroxyl groups.

The reduction in solubility by the addition of a non-ionic polymer, e.g. poly(ethylene glycol), can be prevented by the addition of an additive, e.g. sorbitol.

Thus, one aspect as reported herein is a method for determining the concentration of a non-ionic polymer and an additive for use in an ion exchange chromatography of a polypeptide comprising the following steps:
- determining in solution in the absence of the additive the concentration of the non-ionic polymer at which less than 50% of the polypeptide remain in solution,
- determining in solution in the presence of a concentration of the non-ionic polymer, which has been determine in the previous step, the concentration of the additive at which more than 95% of the polypeptide remain in solution, thereby determining the concentration of a non-ionic polymer and an additive.

In the following Table the dependency of the solubility of an anti-IL17 antibody (10 mg/ml) as an exemplary polypeptide at room temperature on the concentration of added sorbitol as an example of an additive also at different sodium chloride concentrations is shown (10 mM sodium citrate, poly(ethylene glycol) with a molecular weight of about 3,500 Da, pH 5.0).

TABLE

| additive (sorbitol) [wt-%] | sodium chloride [mM] | PEG 3,500 [wt-%] | c(UV280) [mg/ml] | protein conc. [fraction of initial conc.] |
|---|---|---|---|---|
| 0 | 0 | 0 | 10.7 | ~100% |
| 0 | 0 | 5 | 10.6 | ~100% |
| 0 | 0 | 10 | 1.96 | 19.6% |
| 0 | 250 | 0 | 10.3 | ~100% |
| 0 | 250 | 5 | 10.6 | ~100% |
| 0 | 250 | 10 | 1.77 | 17.7% |
| 0 | 500 | 0 | 10.5 | ~100% |
| 0 | 500 | 5 | 10.6 | ~100% |
| 0 | 500 | 10 | 1.57 | 15.7% |
| 7.5 | 0 | 0 | 11.1 | ~100% |
| 7.5 | 0 | 5 | 10.6 | ~100% |
| 7.5 | 0 | 10 | 5.26 | 52.6% |
| 7.5 | 250 | 0 | 10.7 | ~100% |
| 7.5 | 250 | 5 | 10.6 | ~100% |
| 7.5 | 250 | 10 | 5.83 | 58.3% |
| 7.5 | 500 | 0 | 10.7 | ~100% |
| 7.5 | 500 | 5 | 10.6 | ~100% |
| 7.5 | 500 | 10 | 4.66 | 46.6% |
| 15 | 0 | 0 | 10.7 | ~100% |
| 15 | 0 | 5 | 10.8 | ~100% |
| 15 | 0 | 10 | 11.0 | ~100% |
| 15 | 250 | 0 | 10.8 | ~100% |
| 15 | 250 | 5 | 10.7 | ~100% |
| 15 | 250 | 10 | 10.4 | ~100% |
| 15 | 500 | 0 | 10.7 | ~100% |
| 15 | 500 | 5 | 10.6 | ~100% |
| 15 | 500 | 10 | 10.5 | ~100% |

In the following Table the dependency of the solubility of an anti-IL17 antibody (10 mg/ml) and an anti-CSF-1R antibody (10 mg/ml) as an exemplary polypeptides at room temperature on the concentration of added glycerol as an example of an additive is shown (10 mM sodium citrate, poly(ethylene glycol) with MW of 3,500 Da, pH 5.0).

TABLE

| additive (glycerol) [wt-%] | PEG-3,500 [wt-%] | c(UV280) anti-IL17 antibody [mg/ml] | protein conc. anti-IL17 antibody [fraction of initial conc.] | c(UV280) anti-CSF-1R antibody [mg/ml] | protein conc. anti-CSF-1R antibody [fraction of initial conc.] |
|---|---|---|---|---|---|
| 0 | 0 | 9.65 | 96.5% | 9.82 | 98.2% |
| 0 | 5 | 10.0 | 100% | 10.0 | 100% |
| 0 | 10 | 2.13 | 21.3% | 0.59 | 5.9% |
| 7.5 | 0 | 9.76 | 97.6% | 9.96 | 99.6% |
| 7.5 | 5 | 9.88 | 98.8% | 10.2 | ~100% |
| 7.5 | 10 | 3.28 | 32.8% | 1.56 | 15.6% |
| 15 | 0 | 9.82 | 98.2% | 9.88 | 98.8% |
| 15 | 5 | 9.92 | 99.2% | 10.2 | ~100% |
| 15 | 10 | 6.70 | 67.0% | 3.04 | 30.4% |
| 20 | 0 | 9.95 | 99.5% | 10.2 | ~100% |
| 20 | 5 | 9.89 | 98.9% | 10.2 | ~100% |
| 20 | 10 | 8.46 | 84.6% | 5.54 | 55.4% |
| 25 | 0 | 10.3 | ~100% | 9.87 | 98.7% |
| 25 | 5 | 10.0 | 100% | 9.86 | 98.6% |
| 25 | 10 | 9.92 | 99.2% | 8.94 | 89.4% |
| 30 | 0 | 10.1 | ~100% | 9.77 | 97.7% |
| 30 | 5 | 9.92 | 99.2% | 10.1 | ~100% |
| 30 | 10 | 9.85 | 98.5% | 10.0 | 100% |

In the following Table the dependency of the solubility of an anti-IL17 antibody (10 mg/ml) and an anti-CSF-1R antibody (10 mg/ml) as an exemplary polypeptides at room temperature on the concentration of added xylitol as an example of an additive is shown (10 mM sodium citrate, poly(ethylene glycol) with MW of 3,500 Da, pH 5.0).

TABLE

| additive (xylitol) [wt-%] | PEG-3,500 [wt-%] | c(UV280) anti-IL17 antibody [mg/ml] | protein conc. anti-IL17 antibody [fraction of initial conc.] | c(UV280) anti-CSF-1R antibody [mg/ml] | protein conc. anti-CSF-1R antibody [fraction of initial conc.] |
|---|---|---|---|---|---|
| 15 | 0 | 10.1 | ~100% | 10.2 | ~100% |
| 15 | 10 | 9.01 | 90.1% | 5.15 | 51.5% |
| 20 | 0 | 10.2 | ~100% | 10.1 | ~100% |
| 20 | 10 | 10.3 | ~100% | 10.1 | ~100% |

In the following Table the dependency of the solubility of an anti-IL17 antibody (10 mg/ml) and an anti-CSF-1R antibody (10 mg/ml) as an exemplary polypeptides at room temperature on the concentration of added glycine as an example of an additive is shown (10 mM sodium citrate, poly(ethylene glycol) with MW of 3,500 Da, pH 5.0).

TABLE

| additive (glycine) [wt-%] | PEG-3,500 [wt-%] | c(UV280) anti-IL17 antibody [mg/ml] | protein conc. anti-IL17 antibody [fraction of initial conc.] | c(UV280) anti-CSF-1R antibody [mg/ml] | protein conc. anti-CSF-1R antibody [fraction of initial conc.] |
|---|---|---|---|---|---|
| 0 | 0 | 9.82 | 98.2% | 9.94 | 99.4% |
| 0 | 5 | 10.0 | 100% | 10.0 | 100% |
| 0 | 10 | 1.60 | 16.0% | 0.53 | 5.3% |
| 1 | 0 | 9.85 | 98.5% | 9.72 | 97.2% |
| 1 | 10 | 3.80 | 38.0% | 1.49 | 14.9% |
| 2 | 0 | 9.73 | 97.3% | 9.83 | 98.3% |
| 2 | 10 | 7.18 | 71.8% | 3.19 | 31.9% |
| 4 | 0 | 9.84 | 98.4% | 9.77 | 97.7% |
| 4 | 5 | 9.96 | 99.6% | 10.1 | ~100% |
| 4 | 10 | 10.5 | ~100% | 9.71 | 97.1% |
| 8 | 0 | 9.89 | 98.9% | 9.95 | 99.5% |
| 8 | 5 | 9.87 | 98.7% | 9.94 | 99.4% |
| 8 | 10 | 9.90 | 99.0% | 11.3 | ~100% |

In the following Table the dependency of the solubility of an anti-IL17 antibody (10 mg/ml) and an anti-CSF-1R antibody (10 mg/ml) as an exemplary polypeptides at room temperature on the concentration of added proline as an example of an additive is shown (10 mM sodium citrate, poly(ethylene glycol) with MW of 3,500 Da, pH 5.0).

TABLE

| additive (proline) [wt-%] | PEG-3,500 [wt-%] | c(UV280) anti-IL17 antibody [mg/ml] | protein conc. anti-IL17 antibody [fraction of initial conc.] | c(UV280) anti-CSF-1R antibody [mg/ml] | protein conc. anti-CSF-1R antibody [fraction of initial conc.] |
|---|---|---|---|---|---|
| 1 | 0 | 9.74 | 97.4% | 9.75 | 97.5% |
| 1 | 10 | 3.86 | 38.6% | 1.63 | 16.3% |
| 2 | 0 | 9.78 | 97.8% | 9.99 | 99.9% |
| 2 | 10 | 8.38 | 83.8% | 3.61 | 36.1% |
| 4 | 0 | 9.93 | 99.3% | 10.0 | 100% |
| 4 | 10 | 9.85 | 98.5% | 10.1 | >100% |
| 8 | 0 | 9.98 | 99.8% | 10.1 | >100% |
| 8 | 10 | 10.1 | >100% | 10.2 | >100% |

In the following Table the dependency of the solubility of an anti-IL17 antibody (10 mg/ml) and an anti-CSF-1R antibody (10 mg/ml) as an exemplary polypeptides at room temperature on the concentration of added Betaine as an example of an additive is shown (10 mM sodium citrate, poly(ethylene glycol) with MW of 3,500 Da, pH 5.0).

TABLE

| additive (Betaine) [wt-%] | PEG-3,500 [wt-%] | c(UV280) anti-IL17 antibody [mg/ml] | protein conc. anti-IL17 antibody [fraction of initial conc.] | c(UV280) anti-CSF-1R antibody [mg/ml] | protein conc. anti-CSF-1R antibody [fraction of initial conc.] |
|---|---|---|---|---|---|
| 0 | 0 | 9.66 | 96.6% | 9.82 | 98.2% |
| 0 | 5 | 9.81 | 98.1% | 9.97 | 99.7% |
| 0 | 10 | 1.53 | 15.3% | 0.43 | 4.3% |
| 1 | 0 | 9.57 | 95.7% | 9.83 | 98.3% |
| 1 | 10 | 7.11 | 71.1% | 2.28 | 22.8% |
| 2.5 | 0 | 9.60 | 96.0% | 9.60 | 96.0% |
| 2.5 | 10 | 9.68 | 96.8% | 9.89 | 98.9% |
| 5 | 0 | 9.73 | 97.3% | 9.81 | 98.1% |
| 5 | 10 | 9.57 | 95.7% | 10.0 | 100% |
| 7.5 | 0 | 9.65 | 96.5% | 9.86 | 98.6% |
| 7.5 | 5 | 9.98 | 99.8% | 9.99 | 99.9% |
| 7.5 | 10 | 10.5 | ~100% | 10.2 | ~100% |
| 15 | 0 | 9.75 | 97.5% | 9.87 | 98.7% |
| 15 | 5 | 10.1 | ~100% | 10.1 | ~100% |
| 15 | 10 | 10.3 | ~100% | 10.7 | ~100% |

In the following Table the dependency of the solubility of an anti-IL17 antibody (10 mg/ml) and an anti-CSF-1R antibody (10 mg/ml) as an exemplary polypeptides at room temperature on the concentration of added sucrose as an example of an additive is shown (10 mM sodium citrate, poly(ethylene glycol) with MW of 3,500 Da, pH 5.0).

TABLE

| additive (sucrose) [wt-%] | PEG-3,500 [wt-%] | c(UV280) anti-IL17 antibody [mg/ml] | protein conc. anti-IL17 antibody [fraction of initial conc.] | c(UV280) anti-CSF-1R antibody [mg/ml] | protein conc. anti-CSF-1R antibody [fraction of initial conc.] |
|---|---|---|---|---|---|
| 0 | 0 | 9.64 | 96.4% | 9.74 | 97.4% |
| 0 | 5 | 10.0 | 100% | 10.0 | 100% |
| 0 | 10 | 1.63 | 16.3% | 0.66 | 6.6% |
| 7.5 | 0 | 9.56 | 95.6% | 9.76 | 97.6% |
| 7.5 | 5 | 10.2 | ~100% | 10.3 | ~100% |
| 7.5 | 10 | 4.49 | 44.9% | 1.58 | 15.8% |
| 15 | 0 | 9.82 | 98.2% | 9.90 | 99.0% |
| 15 | 5 | 10.4 | ~100% | 10.4 | ~100% |
| 15 | 10 | 7.80 | 78.0% | 3.33 | 33.3% |
| 20 | 0 | 9.71 | 97.1% | 9.80 | 98.0% |
| 20 | 10 | 9.96 | 99.6% | 10.2 | ~100% |
| 25 | 0 | 9.65 | 96.5% | 10.0 | 100% |
| 25 | 10 | 9.73 | 97.3% | 9.95 | 99.5% |

In the following Table the dependency of the solubility of an anti-IL17 antibody (10 mg/ml) and an anti-CSF-1R antibody (10 mg/ml) as an exemplary polypeptides at room temperature on the concentration of added fructose as an example of an additive is shown (10 mM sodium citrate, poly(ethylene glycol) with MW of 3,500 Da, pH 5.0).

TABLE

| additive (fructose) [wt-%] | PEG-3,500 [wt-%] | c(UV280) anti-IL17 antibody [mg/ml] | protein conc. anti-IL17 antibody [fraction of initial conc.] | c(UV280) anti-CSF-1R antibody [mg/ml] | protein conc. anti-CSF-1R antibody [fraction of initial conc.] |
|---|---|---|---|---|---|
| 0 | 0 | 9.79 | 97.9% | 9.56 | 95.6% |
| 0 | 5 | 9.93 | 99.3% | 9.85 | 98.5% |
| 0 | 10 | 0.98 | 9.8% | 0.42 | 4.2% |
| 7.5 | 0 | 9.76 | 97.6% | 9.78 | 97.8% |
| 7.5 | 5 | 9.97 | 99.7% | 10.1 | >100% |
| 7.5 | 10 | 3.85 | 38.5% | 1.42 | 14.2% |
| 15 | 0 | 10.0 | 100% | 9.49 | 94.9% |
| 15 | 5 | 10.1 | >100% | 10.0 | 100% |
| 15 | 10 | 8.23 | 82.3% | 3.76 | 37.6% |
| 20 | 0 | 9.65 | 96.5% | 9.91 | 99.1% |
| 20 | 10 | 9.92 | 99.2% | 10.3 | >100% |
| 25 | 0 | 10.0 | 100% | 9.61 | 96.1% |
| 25 | 10 | 9.99 | 99.9% | 10.3 | >100% |

In the following Table the dependency of the solubility of an anti-IL17 antibody (10 mg/ml) and an anti-CSF-1R antibody (10 mg/ml) as an exemplary polypeptides at room temperature on the concentration of added glucose as an example of an additive is shown (10 mM sodium citrate, poly(ethylene glycol) with MW of 3,500 Da, pH 5.0).

TABLE

| additive (glucose) [wt-%] | PEG-3,500 [wt-%] | c(UV280) anti-IL17 antibody [mg/ml] | protein conc. anti-IL17 antibody [fraction of initial conc.] | c(UV280) anti-CSF-1R antibody [mg/ml] | protein conc. anti-CSF-1R antibody [fraction of initial conc.] |
|---|---|---|---|---|---|
| 7.5 | 0 | 9.84 | 98.4% | 97.8 | 97.8% |
| 7.5 | 10 | 5.35 | 53.5% | 2.39 | 23.9% |
| 15 | 0 | 9.98 | 99.8% | 9.92 | 99.2% |
| 15 | 10 | 9.63 | 96.3% | 5.84 | 58.4% |
| 20 | 0 | 10.1 | ~100% | 10.1 | ~100% |
| 20 | 10 | 10.0 | 100% | 8.08 | 80.8% |
| 25 | 0 | 10.5 | ~100% | 10.4 | ~100% |
| 25 | 10 | 10.4 | ~100% | 10.3 | ~100% |

When a non-ionic polymer is combined with an additive in a method as reported herein an improved resolution value can be achieved. In the following Table the obtained resolution value of a combination of poly (ethylene glycol) 3,500 at a concentration of 10% by weight as an example of a non-ionic polymer and an additive at the listed concentration in a chromatographic separation of an anti-IL17 antibody is shown.

TABLE

| resolution value | anti-IL17 antibody | anti-CSF-1R antibody |
|---|---|---|
| 5% PEG, 3,500 Da MW | 0.75 | 0.66 |
| D-sorbitol, 15 wt-% | 0.85 | 0.86 |
| glycine, 8 wt-% | 0.85 | 0.80 |
| L-proline, 8 wt-% | 0.83 | 0.97 |
| Betaine, 8 wt-% | 0.86 | 0.86 |
| saccharose, 25 wt-% | 0.73 | 0.84 |
| D-fructose, 25 wt-% | 0.79 | 0.91 |
| D-glucose, 25 wt-% | 0.81 | 0.97 |
| xylitol, 20 wt-% | 0.76 | 0.94 |
| glycerol, 30 wt-% | 0.77 | 0.90 |

If 10% by weight of poly (ethylene glycol) is used without an additive the antibody precipitates. Therefore, the reference value in the above table was determined in the presence of 5% by weight of the non-ionic polymer.

In the following Table the change in the host cell protein content and the host cell DNA content of a sample subjected to a method as reported herein is shown. It has to be pointed out that in order to determine of the host cell protein content and the host cell DNA content the fraction size had to be increased which resulted in a reduced resolution value. The elution is effected in all presented examples by increasing the sodium chloride concentration in the mobile phase.

TABLE

| elution conditions | resolution value | HCP reduction by [%] | host cell DNA reduction by [%] |
|---|---|---|---|
| anti-IL17 antibody | | | |
| no non-ionic polymer, no additive | 0.44 | 85.5 | 61.8 |
| 5 wt-% PEG-3,500 | 0.70 | 94.5 | increase |
| 10 wt-% PEG-3,500, 15 wt-% D-sorbitol | 0.78 | 98.4 | increase |
| anti-CSF-1R antibody | | | |
| no non-ionic polymer, no additive | 0.56 | 98.6 | 80.9 |
| 5 wt-% PEG-3,500 | 0.66 | 99.5 | 77.7 |
| 10 wt-% PEG-3,500, 15 wt-% D-sorbitol | 0.88 | 99.7 | 17.0 |

As can be seen from the table above in a chromatographic method comprising a non-ionic polymer and an additive in the recovering solution the HCP (host cell protein) content in the recovered antibody preparation can be reduced compared to methods performed in the absence of this combination.

Thus, one aspect as reported herein is a method for producing an antibody preparation with reduced host cell protein content whereby the preparation is obtained from a mammalian cell cultivation supernatant, especially a CHO cell cultivation supernatant, comprising the following steps:
  applying a solution comprising a non-ionic polymer and an additive to a chromatography material to which an antibody had been adsorbed, whereby the antibody in monomeric form remains adsorbed to an ion exchange chromatography material, and
  recovering the antibody in monomeric form from the ion exchange chromatography material by applying a solution comprising a non-ionic polymer, an additive, and an elution compound, and thereby producing the antibody preparation with reduced host cell protein content.

Another aspect as reported herein is a method for producing an antibody comprising the following steps:
  a) cultivating a mammalian cell comprising a nucleic acid encoding the antibody and recovering the antibody from the cell or the cultivation medium,
  b) purifying the antibody with a cation exchange chromatography method comprising the following steps:
    applying a solution comprising a non-ionic polymer and an additive to a chromatography material to which an antibody had been adsorbed, whereby the antibody in monomeric form remains adsorbed to an ion exchange chromatography material, and
    recovering the antibody in monomeric form from the ion exchange chromatography material by applying a solution comprising a non-ionic polymer, an additive, and an elution compound, and thereby producing the antibody.

In the following Table the resolution values obtained with different cation exchange chromatography materials with an anti-IL17 antibody are shown. The elution is effected in all presented examples by increasing the sodium chloride concentration in the mobile phase.

TABLE

| elution conditions | chromatography material | resolution value |
|---|---|---|
| no non-ionic polymer, no additive | SP Sepharose FF | 0.29 |
| no non-ionic polymer, no additive | Toyopearl CM-650M | 0.53 |
| no non-ionic polymer, no additive | CM Sepharose FF | 0.29 |
| 5 wt-% PEG-3,500 | SP Sepharose FF | 0.45 |
| 5 wt-% PEG-3,500 | Toyopearl CM-650M | 0.67 |
| 5 wt-% PEG-3,500 | CM Sepharose FF | 0.44 |
| 10 wt-% PEG-3,500 15 wt-% D-sorbitol | SP Sepharose FF | 0.51 |
| 10 wt-% PEG-3,500 15 wt-% D-sorbitol | Toyopearl CM-650M | 0.76 |

TABLE-continued

| elution conditions | chromatography material | resolution value |
|---|---|---|
| 10 wt-% PEG-3,500 15 wt-% D-sorbitol | CM Sepharose FF | 0.51 |

In the following Table the resolution values obtained with a method as reported herein using poly (ethylene glycol) 400 Da MW and 10,000 Da MW as non-ionic polymer with different molecular weights and the polyol sorbitol as additive are shown with an anti-IL17 antibody.

TABLE

| elution conditions | resolution value |
|---|---|
| 10 wt-% PEG-400; 15 wt-% D-sorbitol | 0.52 |
| 10 wt-% PEG-400; 15% D-sorbitol | 0.56 |
| 10 wt-% PEG-400; 15% D-sorbitol | 0.57 |
| average: | 0.55 |
| 10 wt-% PEG-10.000; 15% D-sorbitol | 0.58 |
| 10 wt-% PEG-10.000; 15% D-sorbitol | 0.70 |
| 10 wt-% PEG-10.000; 15% D-sorbitol | 0.65 |
| average: | 0.64 |

Depending on the envisaged purity after performing a method as reported herein the recovery of the monomeric polypeptide varies depending on the combination of the concentration of the non-ionic polymer and the additive.

In the following this interrelation is exemplified with poly (ethylene glycol) as non-ionic polymer, sorbitol as additive, and an anti-IL17 antibody as polypeptide.

In the following Table the recovery and the final purity of monomeric anti-IL17 antibody with a purity of at least 99% in the pooled (combined) elution fractions depending on the concentration of poly (ethylene glycol) and sorbitol is shown.

TABLE

| | | sorbitol [wt-%] | | | | | | |
|---|---|---|---|---|---|---|---|---|
| | | 0 | 3 | 5 | 10 | 15 | 20 | 30 | 40 |
| recovery monomer [%] | | | | | | | | | |
| PEG-3,500 [wt-%] | 0 | 82.3 | | | | 77.9 | | | |
| | 5 | 87.0 | | | | 84.5 | | | |
| | 6 | 89.0 | | | | | | | |
| | 8 | 82.7 | | | | | | | |
| | 9 | 86.1 | 92.6 | | | | | | |
| | 10 | 86.1 | | 88.5 | 89.2 | 88.6 | 90.0 | 84.9 | 88.1 |
| | 15 | | | | | 87.1 | | | |
| purity monomer [%] | | | | | | | | | |
| PEG-3,500 [wt-%] | 0 | 99.5 | | | | 99.5 | | | |
| | 5 | 99.3 | | | | 99.3 | | | |
| | 6 | 99.3 | | | | | | | |
| | 8 | 98.9 | | | | | | | |
| | 9 | 99.0 | 99.1 | | | | | | |
| | 10 | 99.1 | | 98.8 | 98.9 | 99.3 | 99.2 | 99.1 | 99.0 |
| | 15 | | | | | 99.2 | | | |

The values for the empty cells were not determined.

In the following Table the recovery and the final purity of monomeric anti-IL17 antibody with a purity of at least 99.5% in the pooled (combined) elution fractions depending on the concentration of poly (ethylene glycol) and sorbitol is shown.

TABLE

| | | sorbitol [wt-%] | | | | | | |
|---|---|---|---|---|---|---|---|---|
| | | 0 | 3 | 5 | 10 | 15 | 20 | 30 | 40 |
| recovery monomer [%] | | | | | | | | | |
| PEG-3,500 [wt-%] | 0 | 82.3 | | | | 77.9 | | | |
| | 5 | 81.3 | | | | 78.7 | | | |
| | 6 | 83.3 | | | | | | | |
| | 8 | 81.1 | | | | | | | |
| | 9 | 84.3 | 92.0 | | | | | | |
| | 10 | 84.9 | | 85.3 | 88.2 | 87.1 | 87.0 | 81.5 | 82.8 |
| | 15 | | | | | 86.0 | | | |
| purity monomer [%] | | | | | | | | | |
| PEG-3,500 [wt-%] | 0 | 99.5 | | | | 99.5 | | | |
| | 5 | 99.8 | | | | 99.9 | | | |
| | 6 | 99.8 | | | | | | | |
| | 8 | 99.8 | | | | | | | |
| | 9 | 99.5 | 99.5 | | | | | | |
| | 10 | 99.5 | | 100.0 | 99.5 | 99.7 | 99.7 | 99.8 | 99.6 |
| | 15 | | | | | 99.5 | | | |

The values for the empty cells were not determined.

In the following Table the recovery and the final purity of monomeric anti-IL17 antibody with a purity of at least 99.9% in the pooled (combined) elution fractions depending on the concentration of poly (ethylene glycol) and sorbitol is shown.

TABLE

| | | sorbitol [wt-%] | | | | | | |
|---|---|---|---|---|---|---|---|---|
| | | 0 | 3 | 5 | 10 | 15 | 20 | 30 | 40 |
| recovery monomer [%] | | | | | | | | | |
| PEG-3,500 [wt-%] | 0 | 66.3 | | | | 63.9 | | | |
| | 5 | 67.9 | | | | 78.7 | | | |
| | 6 | 66.0 | | | | | | | |
| | 8 | 75.1 | | | | | | | |
| | 9 | 76.9 | 89.1 | | | | | | |
| | 10 | 80.4 | | 85.3 | 83.1 | 84.5 | 81.3 | 76.0 | 64.6 |
| | 15 | | | | | 80.9 | | | |
| purity monomer [%] | | | | | | | | | |
| PEG-3,500 [wt-%] | 0 | 99.9 | | | | 100.0 | | | |
| | 5 | 100.0 | | | | 99.9 | | | |
| | 6 | 100.0 | | | | | | | |
| | 8 | 100.0 | | | | | | | |
| | 9 | 99.9 | 99.9 | | | | | | |
| | 10 | 99.9 | | 100.0 | 100.0 | 99.9 | 99.9 | 100.0 | 100.0 |
| | 15 | | | | | 99.9 | | | |

The values for the empty cells were not determined.

In the following Table the recovery and the final purity of monomeric anti-IL17 antibody with a purity of 100% in the pooled (combined) elution fractions depending on the concentration of poly (ethylene glycol) and sorbitol is shown.

TABLE

| | | sorbitol [wt-%] | | | | | | | |
|---|---|---|---|---|---|---|---|---|---|
| | | 0 | 3 | 5 | 10 | 15 | 20 | 30 | 40 |
| recovery monomer [%] | | | | | | | | | |
| PEG-3,500 [wt-%] | 0 | 41.1 | | | | 63.9 | | | |
| | 5 | 67.9 | | | | 67.1 | | | |
| | 6 | 66.0 | | | | | | | |
| | 8 | 75.1 | | | | | | | |
| | 9 | 67.0 | 84.7 | | | | | | |
| | 10 | 75.8 | | 85.3 | 83.1 | 68.7 | 70.5 | 76.0 | 64.6 |
| | 15 | | | | | | 75.5 | | |
| purity monomer [%] | | | | | | | | | |
| PEG-3,500 [wt-%] | 0 | 100.0 | | | | 100.0 | | | |
| | 5 | 100.0 | | | | 100.0 | | | |
| | 6 | 100.0 | | | | | | | |
| | 8 | 100.0 | | | | | | | |
| | 9 | 100.0 | 100.0 | | | | | | |
| | 10 | 100.0 | | 100.0 | 100.0 | 100.0 | 100.0 | 100.0 | 100.0 |
| | 15 | | | | | | 100.0 | | |

The values for the empty cells were not determined.

Generally a chromatographic separation step comprises several sub-steps:
- equilibrating the packed chromatographic material in a chromatography column,
- applying the solution comprising the polypeptide of interest to the equilibrated chromatography material under conditions suitable for the adsorption/binding of the polypeptide of interest to the chromatography material and thereby loading the chromatography column,
- optionally washing the chromatographic material without desorbing/eluting the polypeptide of interest from the chromatographic material,
- recovering the polypeptide of interest by applying a recovering solution to the chromatographic material and thereby desorbing/eluting the polypeptide of interest from the chromatographic material.

In one embodiment the cation exchange chromatography material in the column is equilibrated prior to the applying of the solution comprising the polypeptide to the column. This can be accomplished by applying an equilibration buffer to the column to establish a suitable pH value, and/or conductivity, and/or concentration of salt inside or on the cation exchange chromatography material.

In one embodiment the solution comprising the polypeptide is adjusted to conditions comparable to those to which the cation exchange chromatography column is equilibrated.

Different methods for loading of the chromatography column with the polypeptide of interest are possible. In one embodiment the polypeptide of interest is added to the solution and is loaded onto the column. In another embodiment the polypeptide of interest is added after the column is equilibrated and/or washed. In one embodiment the equilibrating comprises the applying of a binding buffer before loading of the solution onto the chromatographic material.

As outlined above is the method as reported herein performed in bind-and-elute mode.

The recovery of the polypeptide in monomeric form in the method as reported herein can be carried out using a linear gradient, a step gradient, or a combination of a linear and a step gradient. A linear gradient can be, for example, used to further improve the resolution of the polypeptide in monomeric form from the polypeptide in aggregated form and/or from other contaminants such as host cell protein. A step gradient can be used in order to reduce the volume of recovered polypeptide solution. Selection and use of any gradient in the recovery of the polypeptide from the cation exchange chromatography material can easily be made by a person skilled in the art.

In one embodiment the application of the solution comprising the polypeptide is followed by the application of a buffered wash solution to the chromatography material, often of the same composition as the equilibration buffer.

In one embodiment the concentration of the non-ionic polymer is held constant during elution while the pH value is changed and/or the concentration of the salt causing elution is increased.

In one embodiment the concentration of the non-ionic polymer is increased during elution while the pH value is changed and/or the concentration of a salt causing elution is increased.

In one embodiment the concentration of the non-ionic polymer is decreased during elution while the pH value and/or the concentration of the salt are held constant.

After use, the cation exchange chromatography material can be cleaned, sanitized, and stored in an appropriate agent.

The method as reported herein can practiced in combination with one or more other chromatographic steps or methods, such as but not limited to protein A affinity chromatography and other forms of affinity chromatography, hydrophobic interaction chromatography, or other mixed mode chromatography.

The method as reported herein can be practiced in a packed bed column, a fluidized/expanded bed column containing the cation exchange chromatography material, and/or a batch operation where the cation exchange chromatography material is mixed with the polypeptide preparation for a certain time.

The method as reported herein is useful to produce biologically active polypeptides in monomeric form. Such biologically active polypeptides are in one embodiment selected from antibodies, antibody variant, antibody conjugates. In another embodiment the polypeptide of interest is an antibody, especially a monoclonal antibody. The antibody may be from any mammal, such as a mouse, rat, rabbit, guinea pig, sheep, cow, or a transgenic animal with a human immunoglobulin locus, or it may be a humanized, resurfaced, T-cell epitope depleted variant thereof.

It has to be understood that a person skilled in the art can practice the method as reported herein to produce any polypeptide. Thus, an antibody as used herein has to be treated as an example of a polypeptide.

In the method as reported herein different antibody preparation can be used, such as non-purified (crude) or partially purified antibodies from natural, synthetic, or recombinant sources. Crude antibody preparations can be obtained from various sources including, but not limited to, plasma, serum, ascites, or milk of an experimental animal, plant extracts, bacterial cell lysates, yeast lysates, or conditioned animal cell culture media. Partially purified preparations can be obtained from crude preparations that have been subjected to at least one chromatography, precipitation, other fractionation step, or any combination thereof. The precipitation step can include any method, such as salt or poly (ethylene glycol) precipitation. Other fractionation steps such as crystallization or membrane filtration can also be used. In one embodiment the antibody is a not-PEGylated antibody.

With the method as reported herein a polypeptide can be obtained that is substantially free of aggregates. In one embodiment is the content of the polypeptide in aggregated form as determined by size exclusion chromatography less than about 5% based on the total peak area. In another embodiment the content of the polypeptide in aggregated form is less than about 1%. In a further embodiment the amount of the polypeptide in aggregated form is less than about 0.5%. In still another embodiment the amount of the polypeptide in aggregated form is less than about 0.1%.

Recently a new bispecific bivalent antibody format has been published (Proc. Natl. Acad. Sci. USA 108 (2011) 11187-11192), the so called "CrossMab". This bispecific antibody comprises four different antibody chains, i.e. two different light chains and two different heavy chains. During the expression different product-related impurities can be formed. One of these product related impurities is the so called "¾ antibody", an antibody that is missing one light chain, displaying a molecular weight of about 125 kDa compared to a weight of about 150 kDa for a complete four chain antibody. These kinds of antibody-fragments can generally be formed during the expression of antibodies.

Thus, one aspect as reported herein is a method for producing a full length four chain antibody comprising the following steps:

a) cultivating a mammalian cell comprising a nucleic acid encoding the antibody and recovering the antibody from the cell or the cultivation medium, b) purifying the antibody with a cation exchange chromatography method comprising the following steps:
   applying a solution comprising a non-ionic polymer and an additive to a chromatography material to which an antibody had been adsorbed, whereby the four chain full length antibody in monomeric form remains adsorbed to an ion exchange chromatography material, and
   recovering the four chain full length antibody in monomeric form from the ion exchange chromatography material by applying a solution comprising a non-ionic polymer, an additive, and an elution compound, and thereby producing the antibody.

In one embodiment of all aspects as outlined before the ion exchange chromatography material is a cation exchange chromatography material.

In one embodiment of all aspects as outlined before the non-ionic polymer is selected from the group comprising poly (ethylene glycol) (PEG), poly (propylene glycol) (PPG), PEG-PPG copolymers, and triblock copolymers composed of poly (oxypropylene) (poly (propylene oxide)) flanked by poly (oxyethylene) (poly (ethylene oxide)). In one embodiment the non-ionic polymer is poly (ethylene glycol).

In one embodiment of all aspects as outlined before the additive is selected from the group comprising zwitterions, amino acids, urea, urea derivatives, ampholytes, CHAPSO, natural products, sugars, and polyols. In a further embodiment the additive is sorbitol.

In one embodiment of all aspects as outlined before the non-ionic polymer has a concentration of from about 5% to 15% by weight and/or the additive has a concentration of from 3% to 25% by weight.

In one embodiment of all aspects as outlined before the polypeptide is an antibody of class IgG, or IgD, or IgE, or IgA. In another embodiment the polypeptide is an antibody of class IgG, subclass IgG1, or subclass IgG2, or subclass IgG3, or subclass IgG4.

In one embodiment of all aspects as outlined before the method comprises the following steps:
   applying a first solution that optionally comprises a non-ionic polymer and an additive to an ion exchange chromatographic material and thereby equilibrating the ion exchange chromatography material,
   applying a buffered solution comprising the polypeptide to the equilibrated chromatography material and thereby adsorbing the polypeptide to the chromatography material, whereby the solution is essentially free of a non-ionic polymer and an additive,
   applying a buffered solution comprising a non-ionic polymer and an additive to the chromatography material, whereby the polypeptide in monomeric form remains adsorbed to the ion exchange chromatography material, and
   recovering the polypeptide in monomeric form from the ion exchange chromatography material by applying a solution comprising a non-ionic polymer, an additive, and an elution compound. In one embodiment the recovering is by gradient elution.

The following examples and figures are provided to aid the understanding of the present invention, the true scope of which is set forth in the appended claims. It is understood that modifications can be made in the procedures set forth without departing from the spirit of the invention.

FIGURES

FIG. 1 Elution chromatogram of the cation exchange chromatography of the anti-IL17 antibody on the cation exchange chromatography material.

Figure 2:
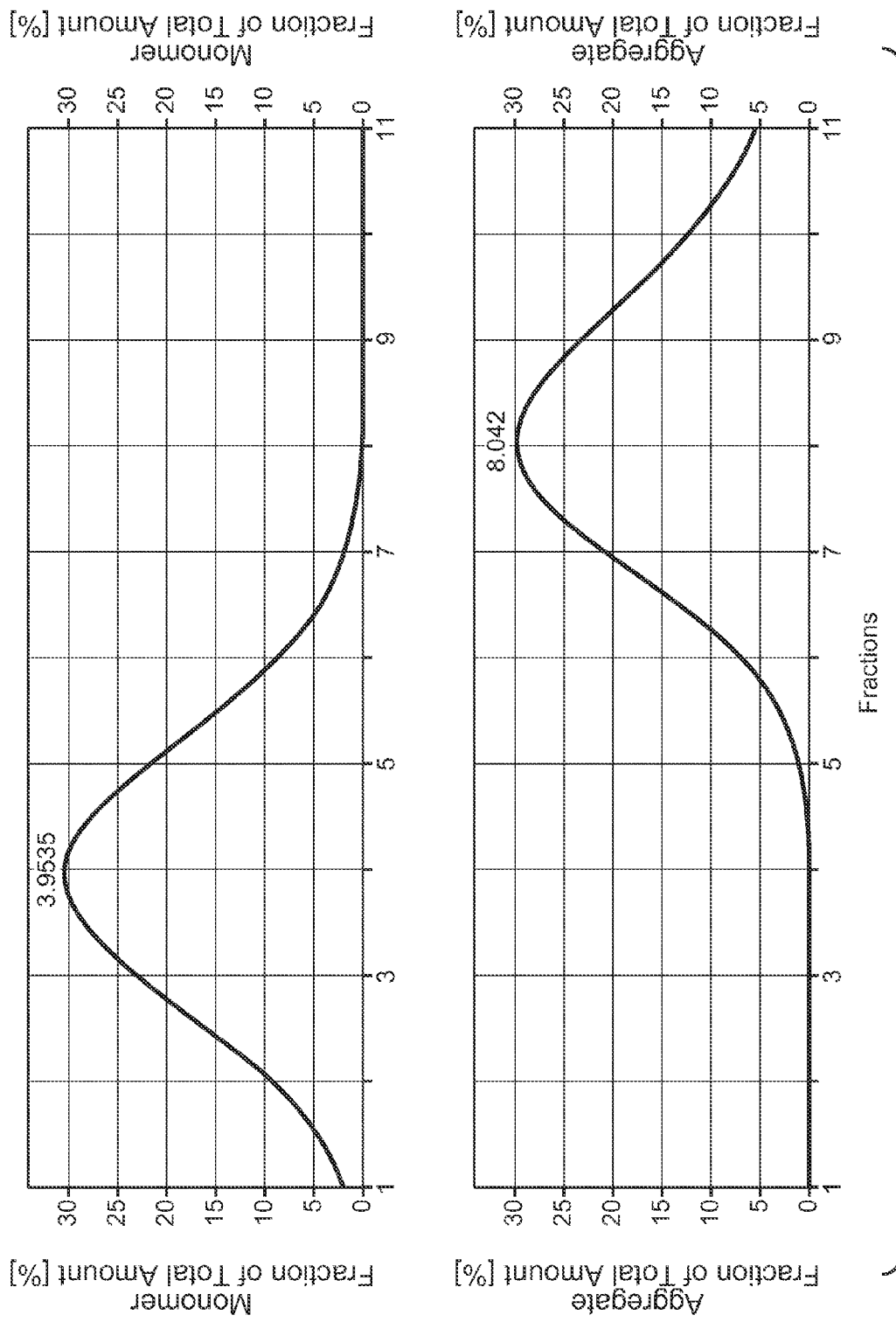

FIG. 2 Distribution of antibody in monomeric form and antibody in aggregated form over the collected fractions.

FIG. 3 Solubility of an anti-IL17 antibody and an anti-CSF-1R antibody in a solution comprising poly (ethylene glycol) 4000 at a concentration of 10% by weight as an example of a non-ionic polymer and different polyols at varying concentration as additive.

FIG. 4 Solubility of an anti-IL17 antibody and an anti-CSF-1R antibody in a solution comprising poly (ethylene glycol) 4000 at a concentration of 10% by weight as an example of a non-ionic polymer and different amino acids at varying concentration as additive.

FIG. 5 Solubility of an anti-IL17 antibody and an anti-CSF-1R antibody in a solution comprising poly (ethylene glycol) at a concentration of 10% by weight as an example of a non-ionic polymer and different sugars at varying concentration as additive.

Figure 6:
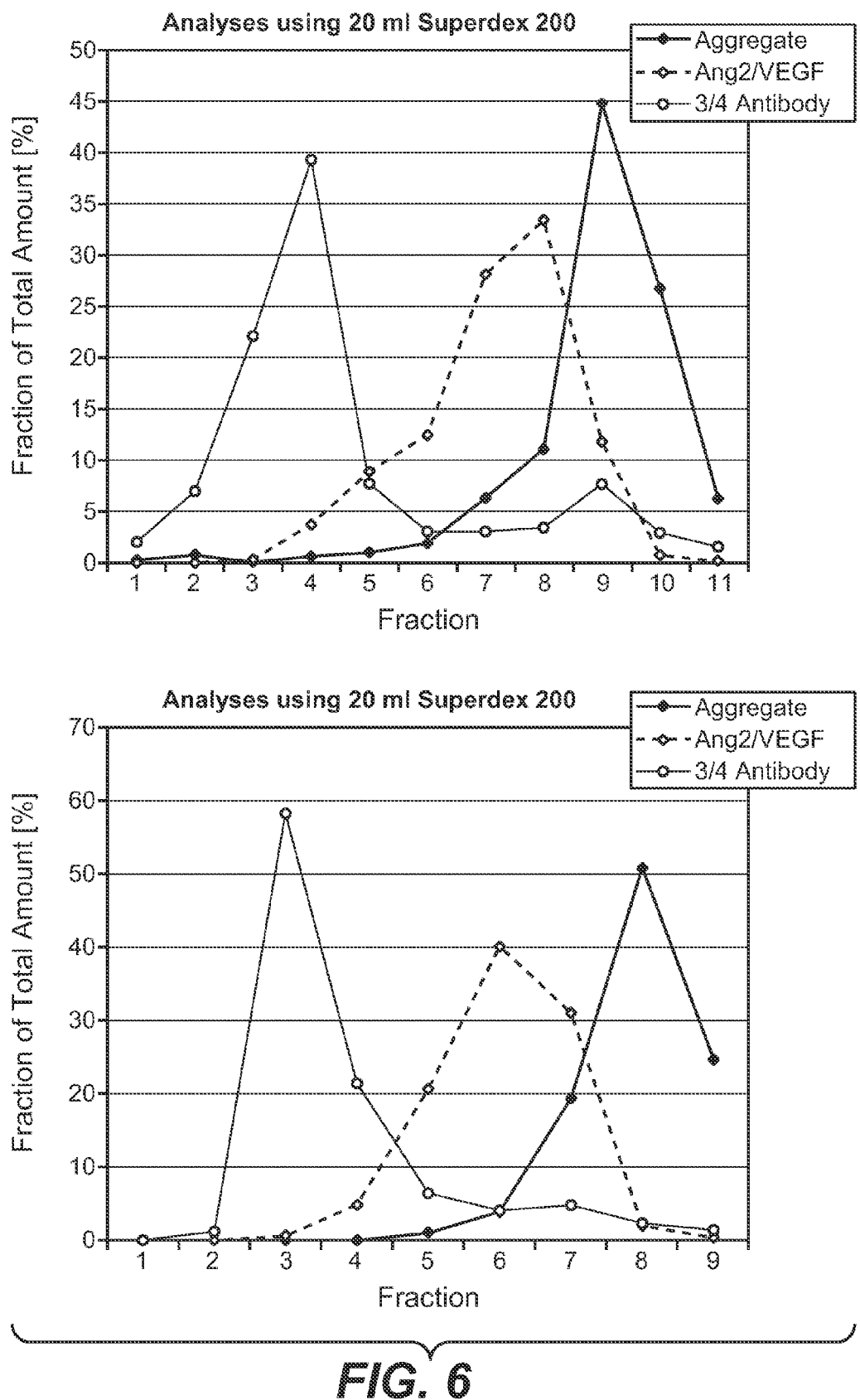

FIG. 6 Distribution of antibody in monomeric form, ¾ antibody fragment and antibody in aggregated form over the collected fractions for examples 25 and 26.

MATERIAL

Each antibody (anti-IL17 antibody: for sequences see WO 2010/034443, anti-CSF-1R antibody: for sequences see PCT/EP2010/069090; anti-Ang2/VEGF antibody: for sequences see WO 2010/040508) was purified in a first step with a protein A affinity chromatography. Elution from the protein A column was carried out under acidic conditions. Afterwards the sample was adjusted to about pH 3.5 with 1 M citric acid and incubated for ~1 hour. Subsequently the pH was adjusted to 5.0 or 5.5 by adding 1 M TRIS/HCl, pH 8-9 or 1 M TRIS solution (TRIS: tris-hydroxymethyl-amino-methane). After incubation at 4° C. for 12-18 hours the sample was depth filtrated. The sample is a solution with a protein concentration between 5 mg/ml and 20 mg/ml. This material is referred to in the following as conditioned protein A eluate, which is prepared for loading onto a cation exchange chromatography material.

The anti-Ang2/VEGF antibody was in addition purified by anion exchange chromatography: The pH value of the conditioned protein A eluate was adjusted to 7.5 by the addition of 1M TRIS buffer solution. Subsequently the sample was processed by anion exchange chromatography at pH 7.5 in flow-through mode.

In the first example the method as reported herein has been carried out. Thus, in Example 1 all conditions of the method are given. In the thereafter following examples only the differences are listed. All not mentioned parameters are identical.

Example 1

Chromatography Conditions

Polypeptide: anti-IL17 antibody
Exchange material: Poros 50HS
Column: 8 mm internal diameter, 100 mm length, 5.03 ml volume
Flow rate: 90 cm/h (=0.75 ml/min)
Equilibration solution: 10 mM sodium citrate buffer, adjusted to pH 5.0, 4 column volumes
Loading: 20 g protein/1 chromatography material
Wash solution 1: 10 mM sodium citrate buffer, adjusted to pH 5.0, 1 column volume
Wash solution 2: 10 mM sodium citrate buffer, 10% (w/w) poly (ethylene glycol) (MW 3,500 Da), 15% (w/w) D-sorbitol, adjusted to pH 5.0
Elution solution: 10 mM sodium citrate buffer, 10% (w/w) poly (ethylene glycol) (MW 3,500 Da), 15% (w/w) D-sorbitol, comprising 750 mM sodium chloride, adjusted to pH 5.0
Elution method: linear gradient from 0% (v/v) to 100% (v/v) elution solution in 22.5 column volumes The conditioned protein A eluate was applied to a chromatography column containing the ion exchange chromatography material. After the loading step at a flow rate of 90 cm/h the column was washed with wash solution 1 (1 column volume) and wash solution 2 (3 column volumes). The antibody in monomeric form was recovered with a linear gradient elution method, whereby the pH value was kept constant and the conductivity was varied (increased) by the addition of sodium chloride.

In FIG. 1 the elution chromatogram of the cation exchange chromatography of the anti-IL17 antibody on the cation exchange chromatography material is shown. The antibody in monomeric form and the antibody in aggregated form are separated.

The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | antibody amount [mg] | antibody monomer (SEC) [%] | antibody aggregate (SEC) [%] |
|---|---|---|---|---|---|
| conditioned protein A eluate | 8.93 | 10.7 | 95.67 | 93.35 | 6.65 |
| flow-through | 0.00 | ~90 | 0.00 | 0 | 0 |
| fraction 1 | 0.45 | 3.0 | 1.35 | 100 | 0 |
| fraction 2 | 2.92 | 3.0 | 8.76 | 100 | 0 |
| fraction 3 | 6.30 | 3.0 | 18.90 | 100 | 0 |
| fraction 4 | 8.45 | 3.0 | 25.35 | 100 | 0 |
| fraction 5 | 6.50 | 3.0 | 19.50 | 99.61 | 0.39 |
| fraction 6 | 2.21 | 3.0 | 6.63 | 89.70 | 10.30 |
| fraction 7 | 1.28 | 3.0 | 3.84 | 53.47 | 46.53 |
| fraction 8 | 1.41 | 3.0 | 4.23 | 36.58 | 63.42 |
| fraction 9 | 0.97 | 3.0 | 2.91 | 30.93 | 69.07 |
| fraction 10 | 0.45 | 3.0 | 1.35 | 18.96 | 81.04 |
| fraction 11 | 0.20 | 3.0 | 0.60 | 20.38 | 79.62 |

| sample | amount of CHO HCP based on amount of antibody [ng/mg] | amount of CHO HCP [ng] | amount of CHO HCDNA based on amount of antibody [pg/mg] | amount of CHO HCDNA [pg] |
|---|---|---|---|---|
| conditioned protein A eluate | 471 | 45,061 | 0.80 | 76.54 |
| flow-through | <5 ng/ml | <15 | <0.4 pg/ml | <1.2 |
| fraction 1 | <18 | <24 | <9 | <12.15 |
| fraction 2 | <2.74 | <24 | <1 | <8.76 |
| fraction 3 | <1.27 | <24 | <0.63 | <11.91 |
| fraction 4 | 0.991 | 25 | <0.96 | <24.34 |
| fraction 5 | 1.394 | 27 | 1 | 19.50 |
| fraction 6 | 7.923 | 53 | 6 | 39.78 |
| fraction 7 | 19 | 73 | 10 | 38.40 |
| fraction 8 | 14 | 59 | 10 | 42.30 |
| fraction 9 | 30 | 87 | 15 | 43.65 |
| fraction 10 | 91 | 123 | 26 | 35.10 |
| fraction 11 | 316 | 190 | 53 | 31.80 |

The resolution of the monomer peak and the aggregate peak was determined using the program PeakFit (Seasolve Software Inc.) to be 0.78.

Example 2

Chromatography Conditions

Polypeptide: anti-CSF-1R antibody

The peak containing the antibody was collected in 3 ml fractions, which were analyzed for monomer and aggregate content. The result of the analysis is presented in the following Table.

TABLE

| sample | concentration (UV280) [mg/ml] E = 1.47 | fraction volume [ml] | antibody amount [mg] | antibody monomer (SEC) [%] | antibody aggregate (SEC) [%] |
|---|---|---|---|---|---|
| conditioned protein A eluate | 12.9 | 7.71 | 99.48 | 99.19 | 0.81 |
| flow-through | 0.00 | ~60 | 0.00 | — | — |
| fraction 1 | 0.99 | 3.00 | 2.97 | 100 | 0 |
| fraction 2 | 5.84 | 3.00 | 17.52 | 100 | 0 |
| fraction 3 | 8.30 | 3.00 | 24.90 | 100 | 0 |
| fraction 4 | 7.87 | 3.00 | 23.61 | 100 | 0 |
| fraction 5 | 5.67 | 3.00 | 17.01 | 100 | 0 |
| fraction 6 | 1.94 | 3.00 | 5.82 | 100 | 0 |
| fraction 7 | 0.58 | 3.00 | 1.74 | 94.21 | 5.79 |
| fraction 8 | 0.41 | 3.00 | 1.23 | 87.79 | 12.21 |
| fraction 9 | 0.23 | 1.50 | 0.35 | 84.58 | 15.42 |

TABLE-continued

| sample | amount of CHO HCP based on amount of antibody [ng/mg] | amount of CHO HCP [ng] | amount of CHO HCDNA based on amount of antibody [pg/mg] | amount of CHO HCDNA [pg] |
|---|---|---|---|---|
| conditioned protein A eluate | 1,260 | 125,345 | 2 | 198.96 |
| flow-through | <5 ng/ml | <15 | <0.4 pg/ml | <1.2 |
| fraction 1 | <8.081 | <24 | <4 | 11.88 |
| fraction 2 | 1.579 | 28 | <0.68 | 70.08 |
| fraction 3 | <0.602 | <15 | <0.48 | 16.93 |
| fraction 4 | <1.017 | <24 | 1 | 11.33 |
| fraction 5 | 2.797 | 48 | 1 | 17.01 |
| fraction 6 | 14 | 81 | 5 | 5.82 |
| fraction 7 | 50 | 87 | 19 | 8.70 |
| fraction 8 | 99 | 122 | 28 | 23.37 |
| fraction 9 | n.a. | n.a. | n.a. | n.a. |

The resolution of the monomer peak and the aggregate peak was determined using the program PeakFit (Seasolve Software Inc.) to be 0.88.

Example 3

Chromatography Conditions

Polypeptide: anti-IL17 antibody
Equilibration solution: 35 mM sodium acetate buffer, 10% (w/w) poly (ethylene glycol) (MW 3,500 Da), 15% (w/w) D-sorbitol adjusted to pH 5.0, 4 column volumes
Loading: 20 g protein/1 chromatography material
Wash solution: 35 mM sodium acetate buffer, 10% (w/w) poly (ethylene glycol) (MW 3,500 Da), 15% (w/w) D-sorbitol adjusted to pH 5.0, 1 column volume
Elution solution: 35 mM sodium acetate buffer, 10% (w/w) poly (ethylene glycol) (MW 3,500 Da), 15% (w/w) D-sorbitol, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | anti-body amount [mg] | antibody monomer (SEC) [%] | antibody aggregate (SEC) [%] |
|---|---|---|---|---|---|
| conditioned protein A eluate | 9.36 | 11.0 | 102.98 | 92.76 | 7.24 |
| flow-through | 0.00 | ~50 | 0.00 | 0 | 0 |
| fraction 1 | 0.43 | 2.0 | 0.86 | 100 | 0 |
| fraction 2 | 2.77 | 2.0 | 5.54 | 100 | 0 |
| fraction 3 | 6.10 | 2.0 | 12.20 | 100 | 0 |
| fraction 4 | 8.02 | 2.0 | 16.04 | 100 | 0 |
| fraction 5 | 8.56 | 2.0 | 17.12 | 100 | 0 |
| fraction 6 | 7.86 | 2.0 | 15.72 | 100 | 0 |
| fraction 7 | 5.59 | 2.0 | 11.18 | 99.77 | 0.23 |
| fraction 8 | 2.74 | 2.0 | 5.48 | 97.75 | 2.25 |
| fraction 9 | 1.34 | 2.0 | 2.68 | 85.98 | 14.02 |
| fraction 10 | 1.13 | 2.0 | 2.26 | 55.26 | 44.74 |
| fraction 11 | 1.31 | 2.0 | 2.62 | 35.5 | 64.5 |
| fraction 12 | 1.41 | 2.0 | 2.82 | 24.86 | 75.14 |
| fraction 13 | 1.18 | 2.0 | 2.36 | 22.22 | 77.78 |
| fraction 14 | 0.79 | 2.0 | 1.58 | 15.47 | 84.53 |
| fraction 15 | 0.48 | 2.0 | 0.96 | 13.63 | 86.37 |
| fraction 16 | 0.29 | 2.0 | 0.58 | 13.73 | 86.27 |
| fraction 17 | 0.18 | 2.0 | 0.36 | 16.03 | 83.97 |

The resolution of the monomer peak and the aggregate peak was determined using the program PeakFit (Seasolve Software Inc.) to be 0.86.

Example 4

Chromatography Conditions

Polypeptide: anti-IL17 antibody
Equilibration solution: 25 mM MES buffer, 10% (w/w) poly (ethylene glycol) (MW 3,500 Da), 15% (w/w) D-sorbitol adjusted to pH 5.5, 4 column volumes
Loading: 20 g protein/1 chromatography material
Wash solution: 35 mM MES buffer, 10% (w/w) poly (ethylene glycol) (MW 3,500 Da), 15% (w/w) D-sorbitol adjusted to pH 5.5, 4 column volumes
Elution solution: 35 mM MES buffer, 10% (w/w) poly (ethylene glycol) (MW 3,500 Da), 15% (w/w) D-sorbitol, comprising 750 mM sodium chloride, adjusted to pH 5.5
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | anti-body amount [mg] | antibody monomer (SEC) [%] | antibody aggregate (SEC) [%] |
|---|---|---|---|---|---|
| conditioned protein A eluate | 9.36 | 10.99 | 102.87 | 92.85 | 7.15 |
| flow-through | 0.00 | ~50 | 0.00 | 0 | 0 |
| fraction 1 | 0.28 | 2.0 | 0.56 | 100 | 0 |
| fraction 2 | 1.45 | 2.0 | 2.90 | 100 | 0 |
| fraction 3 | 4.43 | 2.0 | 8.86 | 100 | 0 |
| fraction 4 | 7.17 | 2.0 | 14.34 | 100 | 0 |
| fraction 5 | 8.90 | 2.0 | 17.80 | 100 | 0 |
| fraction 6 | 8.85 | 2.0 | 17.70 | 100 | 0 |
| fraction 7 | 6.64 | 2.0 | 13.28 | 99.65 | 0.35 |
| fraction 8 | 2.97 | 2.0 | 5.94 | 93.13 | 6.87 |
| fraction 9 | 1.61 | 2.0 | 3.22 | 67.63 | 32.37 |
| fraction 10 | 1.50 | 2.0 | 3.00 | 34.08 | 65.92 |
| fraction 11 | 1.51 | 2.0 | 3.02 | 25.22 | 74.78 |
| fraction 12 | 1.19 | 2.0 | 2.38 | 22.68 | 77.32 |
| fraction 13 | 0.72 | 2.0 | 1.44 | 20.45 | 79.55 |
| fraction 14 | 0.43 | 2.0 | 0.86 | 17.36 | 82.64 |
| fraction 15 | 0.25 | 2.0 | 0.50 | 16.24 | 83.76 |
| fraction 16 | 0.15 | 2.0 | 0.30 | 18.61 | 81.39 |

The resolution of the monomer peak and the aggregate peak was determined using the program PeakFit (Seasolve Software Inc.) to be 0.77.

Example 5

Chromatography Conditions

Polypeptide: anti-IL17 antibody
Exchange material: SP Sepharose FF
Equilibration solution: 30 mM sodium citrate buffer, adjusted to pH 5.0, 4 column volumes
Loading: 20 g protein/l chromatography material
Wash solution 1: 30 mM sodium citrate buffer, adjusted to pH 5.0, 1 column volume
Wash solution 2: 30 mM sodium citrate buffer, 10% (w/w) poly (ethylene glycol) (MW 3,500 Da), 15% (w/w) D-sorbitol, adjusted to pH 5.0
Elution solution: 30 mM sodium citrate buffer, 10% (w/w) poly (ethylene glycol) (MW 3,500 Da), 15% (w/w) D-sorbitol, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | antibody amount [mg] | antibody monomer (SEC) [%] | antibody aggregate (SEC) [%] |
|---|---|---|---|---|---|
| conditioned protein A eluate | 9.36 | 10.7 | 100.07 | 92.90 | 7.10 |
| flow-through | 0.00 | ~50 | 0.00 | — | — |
| fraction 1 | 0.18 | 2.00 | 0.36 | 100 | 0 |
| fraction 2 | 0.74 | 2.00 | 1.48 | 100 | 0 |
| fraction 3 | 1.97 | 2.00 | 3.94 | 100 | 0 |
| fraction 4 | 3.62 | 2.00 | 7.24 | 100 | 0 |
| fraction 5 | 5.15 | 2.00 | 10.30 | 100 | 0 |
| fraction 6 | 6.17 | 2.00 | 12.34 | 99.65 | 0.35 |
| fraction 7 | 6.25 | 2.00 | 12.50 | 99.23 | 0.77 |
| fraction 8 | 5.64 | 2.00 | 11.28 | 98.11 | 1.89 |
| fraction 9 | 4.53 | 2.00 | 9.06 | 96.18 | 3.82 |
| fraction 10 | 3.34 | 2.00 | 6.68 | 92.74 | 7.26 |
| fraction 11 | 2.37 | 2.00 | 4.74 | 85.49 | 14.51 |
| fraction 12 | 1.63 | 2.00 | 3.26 | 77.02 | 22.98 |
| fraction 13 | 1.15 | 2.00 | 2.30 | 63.27 | 36.73 |
| fraction 14 | 0.83 | 2.00 | 1.66 | 48.97 | 51.03 |
| fraction 15 | 0.60 | 2.00 | 1.20 | 36.01 | 63.99 |
| fraction 16 | 0.44 | 2.00 | 0.88 | 25.04 | 74.96 |
| fraction 17 | 0.32 | 2.00 | 0.64 | 19.77 | 80.23 |
| fraction 18 | 0.23 | 2.00 | 0.46 | 17.00 | 83.00 |
| fraction 19 | 0.16 | 2.00 | 0.32 | 16.62 | 83.38 |

The resolution of the monomer peak and the aggregate peak was determined using the program PeakFit (Seasolve Software Inc.) to be 0.51.

Example 6

Chromatography Conditions

Polypeptide: anti-IL17 antibody
Exchange material: Toyopearl CM-650 M
Equilibration solution: 30 mM sodium citrate buffer, adjusted to pH 5.0, 4 column volumes
Loading: 20 g protein/l chromatography material
Wash solution 1: 30 mM sodium citrate buffer, adjusted to pH 5.0, 1 column volume
Wash solution 2: 30 mM sodium citrate buffer, 10% (w/w) poly (ethylene glycol) (MW 3,500 Da), 15% (w/w) D-sorbitol, adjusted to pH 5.0
Elution solution: 30 mM sodium citrate buffer, 10% (w/w) poly (ethylene glycol) (MW 3,500 Da), 15% (w/w) D-sorbitol, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | antibody amount [mg] | antibody monomer (SEC) [%] | antibody aggregate (SEC) [%] |
|---|---|---|---|---|---|
| conditioned protein A eluate | 9.38 | 10.7 | 100.32 | 93.05 | 6.95 |
| flow-through | 0.00 | ~50 | 0.00 | 0 | 0 |
| fraction 1 | 0.58 | 2.00 | 1.16 | 100 | 0 |
| fraction 2 | 1.63 | 2.00 | 3.26 | 100 | 0 |
| fraction 3 | 2.89 | 2.00 | 5.78 | 100 | 0 |
| fraction 4 | 4.13 | 2.00 | 8.26 | 100 | 0 |
| fraction 5 | 5.01 | 2.00 | 10.02 | 100 | 0 |
| fraction 6 | 5.49 | 2.00 | 10.98 | 100 | 0 |
| fraction 7 | 5.58 | 2.00 | 11.16 | 100 | 0 |
| fraction 8 | 5.24 | 2.00 | 10.48 | 100 | 0 |
| fraction 9 | 4.52 | 2.00 | 9.04 | 100 | 0 |
| fraction 10 | 3.48 | 2.00 | 6.96 | 99.29 | 0.71 |
| fraction 11 | 2.41 | 2.00 | 4.82 | 97.27 | 2.73 |
| fraction 12 | 1.58 | 2.00 | 3.16 | 91.13 | 8.87 |
| fraction 13 | 1.15 | 2.00 | 2.30 | 75.73 | 24.27 |
| fraction 14 | 0.99 | 2.00 | 1.98 | 44.16 | 55.84 |
| fraction 15 | 0.94 | 2.00 | 1.88 | 17.21 | 82.79 |
| fraction 16 | 0.88 | 2.00 | 1.76 | 16.96 | 83.04 |
| fraction 17 | 0.75 | 2.00 | 1.50 | 10.07 | 89.93 |
| fraction 18 | 0.58 | 2.00 | 1.16 | 8.64 | 91.36 |
| fraction 19 | 0.43 | 2.00 | 0.86 | 0.85 | 99.15 |
| fraction 20 | 0.31 | 2.00 | 0.62 | 0 | 100 |
| fraction 21 | 0.21 | 2.00 | 0.42 | 0 | 100 |
| fraction 22 | 0.15 | 2.00 | 0.30 | 0 | 100 |

The resolution of the monomer peak and the aggregate peak was determined using the program PeakFit (Seasolve Software Inc.) to be 0.76.

Example 7

Chromatography Conditions

Polypeptide: anti-IL17 antibody
Exchange material: CM Sepharose FF
Equilibration solution: 30 mM sodium citrate buffer, adjusted to pH 5.0, 4 column volumes
Loading: 20 g protein/l chromatography material
Wash solution 1: 30 mM sodium citrate buffer, adjusted to pH 5.0, 1 column volume
Wash solution 2: 30 mM sodium citrate buffer, 10% (w/w) poly (ethylene glycol) (MW 3,500 Da), 15% (w/w) D-sorbitol, adjusted to pH 5.0
Elution solution: 30 mM sodium citrate buffer, 10% (w/w) poly (ethylene glycol) (MW 3,500 Da), 15% (w/w) D-sorbitol, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | anti-body amount [mg] | antibody monomer (SEC) [%] | antibody aggregate (SEC) [%] |
|---|---|---|---|---|---|
| conditioned protein A eluate | 9.55 | 10.7 | 102.02 | 93.04 | 6.96 |
| flow-through | 0.00 | ~50 | 0.00 | — | — |
| fraction 1 | 0.14 | 2.00 | 0.28 | 98.77 | 1.23 |
| fraction 2 | 0.47 | 2.00 | 0.94 | 100 | 0 |
| fraction 3 | 1.16 | 2.00 | 2.32 | 100 | 0 |
| fraction 4 | 2.19 | 2.00 | 4.38 | 100 | 0 |
| fraction 5 | 3.32 | 2.00 | 6.64 | 100 | 0 |
| fraction 6 | 4.38 | 2.00 | 8.76 | 100 | 0 |
| fraction 7 | 4.98 | 2.00 | 9.96 | 99.79 | 0.21 |
| fraction 8 | 5.37 | 2.00 | 10.74 | 99.48 | 0.52 |
| fraction 9 | 5.18 | 2.00 | 10.36 | 98.65 | 1.35 |
| fraction 10 | 4.61 | 2.00 | 9.22 | 98.21 | 1.79 |
| fraction 11 | 3.89 | 2.00 | 7.78 | 96.20 | 3.80 |
| fraction 12 | 3.01 | 2.00 | 6.02 | 93.77 | 6.23 |
| fraction 13 | 2.35 | 2.00 | 4.70 | 89.37 | 10.63 |
| fraction 14 | 1.76 | 2.00 | 3.52 | 83.97 | 16.03 |
| fraction 15 | 1.30 | 2.00 | 2.60 | 75.39 | 24.61 |
| fraction 16 | 0.98 | 2.00 | 1.96 | 63.61 | 36.39 |
| fraction 17 | 0.74 | 2.00 | 1.48 | 51.68 | 48.32 |
| fraction 18 | 0.57 | 2.00 | 1.14 | 37.62 | 62.38 |
| fraction 19 | 0.44 | 2.00 | 0.88 | 30.42 | 69.58 |
| fraction 20 | 0.33 | 2.00 | 0.66 | 22.95 | 77.05 |
| fraction 21 | 0.23 | 2.00 | 0.46 | 21.01 | 78.99 |
| fraction 22 | 0.19 | 2.00 | 0.38 | 16.76 | 83.24 |
| fraction 23 | 0.15 | 2.00 | 0.30 | 15.29 | 84.71 |

The resolution of the monomer peak and the aggregate peak was determined using the program PeakFit (Seasolve Software Inc.) to be 0.51.

Example 8

Chromatography Conditions

Polypeptide: anti-IL 17 antibody
Equilibration solution: 10 mM sodium citrate buffer, 10% (w/w) poly (ethylene glycol) (MW 3,500 Da), 20% (w/w) xylitol adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 20% (w/w) xylitol adjusted to pH 5.0, 4 column volume
Elution solution: 10 mM sodium citrate buffer, 10% (w/w) poly (ethylene glycol) (MW 3,500 Da), 20% (w/w) xylitol, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 9.36 | 10.77 | 100.24 | 94.23 | 5.77 | 0 |
| flow-through | 0.00 | ~80 | 0.00 | — | — | 0 |
| fraction 1 | 0.62 | 1.5 | 0.93 | 82.66 | 0 | 17.34 |
| fraction 2 | 2.85 | 1.5 | 4.28 | 100 | 0 | 0 |
| fraction 3 | 5.59 | 1.5 | 8.39 | 100 | 0 | 0 |
| fraction 4 | 7.15 | 1.5 | 10.73 | 100 | 0 | 0 |
| fraction 5 | 7.89 | 1.5 | 11.84 | 100 | 0 | 0 |
| fraction 6 | 7.81 | 1.5 | 11.72 | 100 | 0 | 0 |
| fraction 7 | 7.31 | 1.5 | 10.97 | 100 | 0 | 0 |
| fraction 8 | 6.21 | 1.5 | 9.32 | 100 | 0 | 0 |
| fraction 9 | 4.48 | 1.5 | 6.72 | 99.78 | 0.22 | 0 |
| fraction 10 | 2.74 | 1.5 | 4.11 | 98.36 | 1.64 | 0 |
| fraction 11 | 1.65 | 1.5 | 2.48 | 94.44 | 5.56 | 0 |
| fraction 12 | 1.24 | 1.5 | 1.86 | 77.49 | 22.51 | 0 |
| fraction 13 | 1.23 | 1.5 | 1.85 | 57.48 | 42.52 | 0 |
| fraction 14 | 1.39 | 1.5 | 2.09 | 43.27 | 56.73 | 0 |
| fraction 15 | 1.43 | 1.5 | 2.15 | 36.42 | 63.58 | 0 |
| fraction 16 | 1.30 | 1.5 | 1.95 | 34.12 | 65.88 | 0 |
| fraction 17 | 1.01 | 1.5 | 1.52 | 29.98 | 70.02 | 0 |
| fraction 18 | 0.72 | 1.5 | 1.08 | 23.98 | 76.02 | 0 |
| fraction 19 | 0.48 | 1.5 | 0.72 | 26.01 | 73.99 | 0 |
| fraction 20 | 0.32 | 1.5 | 0.48 | 20.98 | 79.02 | 0 |

TABLE-continued

| sample | concentration (UV280) [mg/ml] E = 1.45 | fraction volume [ml] | antibody amount [mg] | antibody monomer (SEC) [%] | antibody aggregate (SEC) [%] | antibody fragments (SEC) [%] |
|---|---|---|---|---|---|---|
| fraction 21 | 0.22 | 1.5 | 0.33 | 20.23 | 79.77 | 0 |
| fraction 22 | 0.15 | 1.5 | 0.23 | 21.64 | 78.36 | 0 |

The resolution of the monomer peak and the aggregate peak was determined using the program PeakFit (Seasolve Software Inc.) to be 0.76.

Example 9

Chromatography Conditions

Polypeptide: anti-CSF-1R antibody
Equilibration solution: 10 mM sodium citrate buffer, 10% (w/w) poly (ethylene glycol) (MW 3,500 Da), 20% (w/w) xylitol adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 20% (w/w) xylitol adjusted to pH 5.0, 4 column volume
Elution solution: 10 mM sodium citrate buffer, 10% (w/w) poly (ethylene glycol) (MW 3,500 Da), 20% (w/w) xylitol, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

The resolution of the monomer peak and the aggregate peak was determined using the program PeakFit (Seasolve Software Inc.) to be 0.93.

Example 10

Chromatography Conditions

Polypeptide: anti-IL17 antibody
Equilibration solution: 10 mM sodium citrate buffer, 10% (w/w) poly (ethylene glycol) (MW 3,500 Da), 30% (w/w) glycerol adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 30% (w/w) glycerol adjusted to pH 5.0, 4 column volume
Elution solution: 10 mM sodium citrate buffer, 10% (w/w) poly (ethylene glycol) (MW 3,500 Da), 30% (w/w) glycerol, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.47 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 13.3 | 7.41 | 98.58 | 99.19 | 0.81 | 0 |
| flow-through | 0.00 | ~80 | 0.00 | 0 | 0 | 0 |
| fraction 1 | 1.74 | 1.5 | 2.61 | 100 | 0 | 0 |
| fraction 2 | 4.90 | 1.5 | 7.35 | 100 | 0 | 0 |
| fraction 3 | 6.98 | 1.5 | 10.47 | 100 | 0 | 0 |
| fraction 4 | 7.83 | 1.5 | 11.75 | 100 | 0 | 0 |
| fraction 5 | 7.96 | 1.5 | 11.94 | 100 | 0 | 0 |
| fraction 6 | 7.69 | 1.5 | 11.54 | 100 | 0 | 0 |
| fraction 7 | 7.20 | 1.5 | 10.80 | 100 | 0 | 0 |
| fraction 8 | 6.37 | 1.5 | 9.56 | 100 | 0 | 0 |
| fraction 9 | 4.73 | 1.5 | 7.10 | 100 | 0 | 0 |
| fraction 10 | 3.14 | 1.5 | 4.71 | 100 | 0 | 0 |
| fraction 11 | 1.78 | 1.5 | 2.67 | 99.57 | 0.43 | 0 |
| fraction 12 | 0.89 | 1.5 | 1.34 | 98.06 | 1.94 | 0 |
| fraction 13 | 0.64 | 1.5 | 0.96 | 91.40 | 8.60 | 0 |
| fraction 14 | 0.57 | 1.5 | 0.86 | 70.19 | 21.01 | 8.80 |
| fraction 15 | 0.55 | 1.5 | 0.83 | 63.04 | 28.85 | 8.11 |
| fraction 16 | 0.43 | 1.5 | 0.65 | 58.67 | 31.48 | 9.85 |
| fraction 17 | 0.28 | 1.5 | 0.42 | 57.19 | 34.17 | 8.64 |

TABLE

| sample | concentration (UV280) [mg/ml] E = 1.45 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 9.36 | 10.69 | 100.04 | 93.93 | 6.07 | 0 |
| flow-through | 0.00 | ~80 | 0.00 | 0 | 0 | 0 |
| fraction 1 | 0.92 | 1.5 | 1.38 | 66.77 | 0 | 33.23 |
| fraction 2 | 2.90 | 1.5 | 4.35 | 100 | 0 | 0 |
| fraction 3 | 5.06 | 1.5 | 7.59 | 100 | 0 | 0 |
| fraction 4 | 6.36 | 1.5 | 9.54 | 100 | 0 | 0 |
| fraction 5 | 6.71 | 1.5 | 10.07 | 100 | 0 | 0 |
| fraction 6 | 6.74 | 1.5 | 10.11 | 100 | 0 | 0 |
| fraction 7 | 6.45 | 1.5 | 9.68 | 100 | 0 | 0 |
| fraction 8 | 5.71 | 1.5 | 8.57 | 100 | 0 | 0 |
| fraction 9 | 4.70 | 1.5 | 7.05 | 99.84 | 0.16 | 0 |
| fraction 10 | 3.50 | 1.5 | 5.25 | 99.54 | 0.46 | 0 |
| fraction 11 | 2.40 | 1.5 | 3.60 | 98.34 | 1.66 | 0 |
| fraction 12 | 1.61 | 1.5 | 2.42 | 94.80 | 5.20 | 0 |
| fraction 13 | 1.23 | 1.5 | 1.85 | 86.37 | 13.63 | 0 |
| fraction 14 | 1.16 | 1.5 | 1.74 | 66.30 | 33.70 | 0 |
| fraction 15 | 1.28 | 1.5 | 1.92 | 48.88 | 51.12 | 0 |
| fraction 16 | 1.38 | 1.5 | 2.07 | 30.96 | 69.04 | 0 |
| fraction 17 | 1.34 | 1.5 | 2.01 | 29.30 | 70.70 | 0 |
| fraction 18 | 0.88 | 1.5 | 1.32 | 30.99 | 69.01 | 0 |
| fraction 19 | 0.89 | 1.5 | 1.34 | 27.69 | 72.33 | 0 |
| fraction 20 | 0.64 | 1.5 | 0.96 | 31.36 | 68.64 | 0 |
| fraction 21 | 0.56 | 1.5 | 0.84 | 30.76 | 69.24 | 0 |
| fraction 22 | 0.35 | 1.5 | 0.53 | 29.23 | 70.77 | 0 |
| fraction 23 | 0.25 | 1.5 | 0.38 | 27.83 | 72.17 | 0 |
| fraction 24 | 0.18 | 1.5 | 0.27 | 27.50 | 72.50 | 0 |

The resolution of the monomer peak and the aggregate peak was determined using the program PeakFit (Seasolve Software Inc.) to be 0.77.

Example 11

Chromatography Conditions

Polypeptide: anti-CSF-1R antibody
Equilibration solution: 10 mM sodium citrate buffer, 10% (w/w) poly (ethylene glycol) (MW 3,500 Da), 30% (w/w) glycerol adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 30% (w/w) glycerol adjusted to pH 5.0, 4 column volume
Elution solution: 10 mM sodium citrate buffer, 10% (w/w) poly (ethylene glycol) (MW 3,500 Da), 30% (w/w) glycerol, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.47 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 13.3 | 7.55 | 100.64 | 99.13 | 0.87 | 0 |
| flow-through | 0.00 | ~80 | 0.00 | 0 | 0 | 0 |
| fraction 1 | 1.27 | 1.5 | 1.91 | 81.59 | 0 | 18.41 |
| fraction 2 | 3.61 | 1.5 | 5.42 | 100 | 0 | 0 |
| fraction 3 | 5.45 | 1.5 | 8.18 | 100 | 0 | 0 |
| fraction 4 | 6.36 | 1.5 | 9.54 | 100 | 0 | 0 |
| fraction 5 | 6.48 | 1.5 | 9.72 | 100 | 0 | 0 |
| fraction 6 | 6.50 | 1.5 | 9.75 | 100 | 0 | 0 |
| fraction 7 | 6.28 | 1.5 | 9.42 | 100 | 0 | 0 |
| fraction 8 | 5.79 | 1.5 | 8.69 | 100 | 0 | 0 |
| fraction 9 | 5.17 | 1.5 | 7.76 | 100 | 0 | 0 |
| fraction 10 | 4.25 | 1.5 | 6.38 | 100 | 0 | 0 |
| fraction 11 | 3.26 | 1.5 | 4.89 | 100 | 0 | 0 |
| fraction 12 | 2.27 | 1.5 | 3.41 | 99.85 | 0.15 | 0 |
| fraction 13 | 1.43 | 1.5 | 2.15 | 93.21 | 0.35 | 6.45 |
| fraction 14 | 0.86 | 1.5 | 1.29 | 69.58 | 1.24 | 29.18 |
| fraction 15 | 0.60 | 1.5 | 0.90 | 58.01 | 5.92 | 36.07 |

TABLE-continued

| sample | concentration (UV280) [mg/ml] E = 1.47 | fraction volume [ml] | antibody amount [mg] | antibody monomer (SEC) [%] | antibody aggregate (SEC) [%] | antibody fragments (SEC) [%] |
|---|---|---|---|---|---|---|
| fraction 16 | 0.51 | 1.5 | 0.77 | 51.57 | 15.49 | 32.94 |
| fraction 17 | 0.50 | 1.5 | 0.75 | 46.54 | 26.33 | 27.14 |
| fraction 18 | 0.45 | 1.5 | 0.68 | 43.00 | 31.02 | 25.97 |
| fraction 19 | 0.43 | 1.5 | 0.65 | 36.82 | 38.46 | 24.72 |
| fraction 20 | 0.27 | 1.5 | 0.41 | 37.11 | 38.01 | 24.87 |

The resolution of the monomer peak and the aggregate peak was determined using the program PeakFit (Seasolve Software Inc.) to be 0.90.

Example 12

Chromatography Conditions

Polypeptide: anti-IL17 antibody
Equilibration solution: 10 mM sodium citrate buffer, 10% (w/w) poly (ethylene glycol) (MW 3,500 Da), 25% (w/w) saccharose adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 25% (w/w) saccharose adjusted to pH 5.0, 4 column volume
Elution solution: 10 mM sodium citrate buffer, 10% (w/w) poly (ethylene glycol) (MW 3,500 Da), 25% (w/w) saccharose, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 9.36 | 10.71 | 96.91 | 94.97 | 5.03 | 0 |
| flow-through | 0.00 | ~90 | 0.00 | 0 | 0 | 0 |
| fraction 1 | 1.12 | 1.5 | 1.68 | 93.40 | 0 | 6.60 |
| fraction 2 | 3.57 | 1.5 | 5.36 | 100 | 0 | 0 |
| fraction 3 | 6.05 | 1.5 | 9.08 | 100 | 0 | 0 |
| fraction 4 | 7.44 | 1.5 | 11.16 | 100 | 0 | 0 |
| fraction 5 | 7.8 | 1.5 | 11.70 | 100 | 0 | 0 |
| fraction 6 | 7.64 | 1.5 | 11.46 | 100 | 0 | 0 |
| fraction 7 | 6.96 | 1.5 | 10.44 | 100 | 0 | 0 |
| fraction 8 | 5.89 | 1.5 | 8.84 | 100 | 0 | 0 |
| fraction 9 | 4.35 | 1.5 | 6.53 | 99.82 | 0.18 | 0 |
| fraction 10 | 2.85 | 1.5 | 4.28 | 98.95 | 1.05 | 0 |
| fraction 11 | 1.81 | 1.5 | 2.72 | 95.18 | 4.82 | 0 |
| fraction 12 | 1.33 | 1.5 | 2.00 | 85.83 | 14.17 | 0 |
| fraction 13 | 1.23 | 1.5 | 1.85 | 70.44 | 29.56 | 0 |
| fraction 14 | 1.26 | 1.5 | 1.89 | 59.07 | 40.93 | 0 |
| fraction 15 | 1.2 | 1.5 | 1.80 | 50.95 | 49.05 | 0 |
| fraction 16 | 1.01 | 1.5 | 1.52 | 43.67 | 56.33 | 0 |
| fraction 17 | 0.77 | 1.5 | 1.16 | 42.33 | 57.67 | 0 |
| fraction 18 | 0.53 | 1.5 | 0.80 | 36.74 | 63.26 | 0 |
| fraction 19 | 0.36 | 1.5 | 0.54 | 37.68 | 62.32 | 0 |
| fraction 20 | 0.25 | 1.5 | 0.38 | 36.00 | 64.00 | 0 |
| fraction 21 | 0.18 | 1.5 | 0.27 | 34.41 | 65.59 | 0 |

The resolution of the monomer peak and the aggregate peak was determined using the program PeakFit (Seasolve Software Inc.) to be 0.73.

Example 13

Chromatography Conditions

Polypeptide: anti-CSF-1R antibody
Equilibration solution: 10 mM sodium citrate buffer, 10% (w/w) poly (ethylene glycol) (MW 3,500 Da), 25% (w/w) saccharose adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 25% (w/w) saccharose adjusted to pH 5.0, 4 column volume
Elution solution: 10 mM sodium citrate buffer, 10% (w/w) poly (ethylene glycol) (MW 3,500 Da), 25% (w/w) saccharose, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.47 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 13.8 | 7.55 | 100.44 | 99.23 | 0.77 | 0 |
| flow-through | 0.00 | ~90 | 0.00 | 0 | 0 | 0 |
| fraction 1 | 1.78 | 1.5 | 2.67 | 100 | 0 | 0 |
| fraction 2 | 4.54 | 1.5 | 6.81 | 100 | 0 | 0 |
| fraction 3 | 6.45 | 1.5 | 9.68 | 100 | 0 | 0 |
| fraction 4 | 7.46 | 1.5 | 11.19 | 100 | 0 | 0 |
| fraction 5 | 7.50 | 1.5 | 11.25 | 100 | 0 | 0 |
| fraction 6 | 7.35 | 1.5 | 11.03 | 100 | 0 | 0 |
| fraction 7 | 6.79 | 1.5 | 10.19 | 100 | 0 | 0 |
| fraction 8 | 6.01 | 1.5 | 9.02 | 100 | 0 | 0 |
| fraction 9 | 4.87 | 1.5 | 7.31 | 100 | 0 | 0 |
| fraction 10 | 3.63 | 1.5 | 5.45 | 100 | 0 | 0 |
| fraction 11 | 2.38 | 1.5 | 3.57 | 100 | 0 | 0 |
| fraction 12 | 1.41 | 1.5 | 2.12 | 99.73 | 0.27 | 0 |
| fraction 13 | 0.84 | 1.5 | 1.26 | 98.71 | 1.29 | 0 |
| fraction 14 | 0.60 | 1.5 | 0.90 | 83.46 | 5.09 | 11.45 |
| fraction 15 | 0.52 | 1.5 | 0.78 | 74.12 | 9.89 | 15.99 |
| fraction 16 | 0.44 | 1.5 | 0.66 | 71.45 | 11.73 | 16.82 |
| fraction 17 | 0.33 | 1.5 | 0.50 | 70.55 | 13.67 | 15.77 |
| fraction 18 | 0.22 | 1.5 | 0.33 | 61.41 | 14.38 | 24.21 |

The resolution of the monomer peak and the aggregate peak was determined using the program PeakFit (Seasolve Software Inc.) to be 0.84.

Example 14

Chromatography Conditions

Polypeptide: anti-IL17 antibody
Equilibration solution: 10 mM sodium citrate buffer, 10% (w/w) poly (ethylene glycol) (MW 3,500 Da), 25% (w/w) D-fructose adjusted to pH 5.0, 2 column volumes
Loading: 20 g protein/l chromatography material
Wash solution: 10 mM sodium citrate buffer, 10% (w/w) poly (ethylene glycol) (MW 3,500 Da), 25% (w/w) D-fructose adjusted to pH 5.0, 4 column volume
Elution solution: 10 mM sodium citrate buffer, 10% (w/w) poly (ethylene glycol) (MW 3,500 Da), 25% (w/w) D-fructose, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 9.36 | 10.7 | 100.18 | 95.11 | 4.89 | 0 |
| flow-through | 0.00 | ~80 | 0.00 | 0 | 0 | 0 |
| fraction 1 | 0.93 | 1.5 | 1.40 | 79.49 | 0 | 20.51 |
| fraction 2 | 3.94 | 1.5 | 5.91 | 100 | 0 | 0 |
| fraction 3 | 6.68 | 1.5 | 10.02 | 100 | 0 | 0 |
| fraction 4 | 7.86 | 1.5 | 11.79 | 100 | 0 | 0 |
| fraction 5 | 7.98 | 1.5 | 11.97 | 100 | 0 | 0 |
| fraction 6 | 7.52 | 1.5 | 11.28 | 100 | 0 | 0 |
| fraction 7 | 6.83 | 1.5 | 10.25 | 100 | 0 | 0 |
| fraction 8 | 5.75 | 1.5 | 8.63 | 100 | 0 | 0 |
| fraction 9 | 4.45 | 1.5 | 6.68 | 99.78 | 0.22 | 0 |
| fraction 10 | 3.08 | 1.5 | 4.62 | 99.45 | 0.55 | 0 |
| fraction 11 | 1.97 | 1.5 | 2.96 | 97.64 | 2.36 | 0 |
| fraction 12 | 1.39 | 1.5 | 2.09 | 92.02 | 7.98 | 0 |
| fraction 13 | 1.06 | 1.5 | 1.59 | 78.43 | 21.57 | 0 |
| fraction 14 | 1.13 | 1.5 | 1.70 | 59.36 | 40.64 | 0 |
| fraction 15 | 1.24 | 1.5 | 1.86 | 44.05 | 55.95 | 0 |
| fraction 16 | 1.18 | 1.5 | 1.77 | 37.20 | 62.80 | 0 |
| fraction 17 | 1.08 | 1.5 | 1.62 | 32.47 | 67.53 | 0 |
| fraction 18 | 0.76 | 1.5 | 1.14 | 29.88 | 70.12 | 0 |
| fraction 19 | 0.67 | 1.5 | 1.01 | 35.55 | 64.45 | 0 |
| fraction 20 | 0.41 | 1.5 | 0.62 | 28.90 | 71.10 | 0 |

TABLE-continued

| sample | concentration (UV280) [mg/ml] E = 1.45 | fraction volume [ml] | antibody amount [mg] | antibody monomer (SEC) [%] | antibody aggregate (SEC) [%] | antibody fragments (SEC) [%] |
|---|---|---|---|---|---|---|
| fraction 21 | 0.29 | 1.5 | 0.44 | 25.31 | 74.69 | 0 |
| fraction 22 | 0.21 | 1.5 | 0.32 | 23.60 | 76.40 | 0 |
| fraction 23 | 0.20 | 1.5 | 0.30 | 46.16 | 53.84 | 0 |

The resolution of the monomer peak and the aggregate peak was determined using the program PeakFit (Seasolve Software Inc.) to be 0.79.

Example 15

Chromatography Conditions

Polypeptide: anti-CSF-1R antibody
Equilibration solution: 10 mM sodium citrate buffer, 10% (w/w) poly (ethylene glycol) (MW 3,500 Da), 25% (w/w) D-fructose adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 25% (w/w) D-fructose adjusted to pH 5.0, 4 column volume
Elution solution: 10 mM sodium citrate buffer, 10% (w/w) poly (ethylene glycol) (MW 3,500 Da), 25% (w/w) D-fructose, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.47 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 13.3 | 7.55 | 100.43 | 99.22 | 0.78 | 0 |
| flow-through | 0.00 | ~80 | 0.00 | 0 | 0 | 0 |
| fraction 1 | 0.54 | 1.5 | 0.81 | 77.09 | 0.22 | 22.69 |
| fraction 2 | 2.58 | 1.5 | 3.87 | 100 | 0 | 0 |
| fraction 3 | 5.32 | 1.5 | 7.98 | 100 | 0 | 0 |
| fraction 4 | 7.29 | 1.5 | 10.94 | 100 | 0 | 0 |
| fraction 5 | 7.78 | 1.5 | 11.67 | 100 | 0 | 0 |
| fraction 6 | 7.96 | 1.5 | 11.94 | 100 | 0 | 0 |
| fraction 7 | 7.72 | 1.5 | 11.58 | 100 | 0 | 0 |
| fraction 8 | 6.87 | 1.5 | 10.31 | 100 | 0 | 0 |
| fraction 9 | 6.10 | 1.5 | 9.15 | 100 | 0 | 0 |
| fraction 10 | 4.87 | 1.5 | 7.31 | 100 | 0 | 0 |
| fraction 11 | 3.61 | 1.5 | 5.42 | 100 | 0 | 0 |
| fraction 12 | 2.17 | 1.5 | 3.26 | 99.89 | 0.11 | 0 |
| fraction 13 | 1.27 | 1.5 | 1.91 | 99.24 | 0.76 | 0 |
| fraction 14 | 0.81 | 1.5 | 1.22 | 89.35 | 4.06 | 6.58 |
| fraction 15 | 0.63 | 1.5 | 0.95 | 80.84 | 11.62 | 7.54 |
| fraction 16 | 0.59 | 1.5 | 0.89 | 72.37 | 20.76 | 6.86 |
| fraction 17 | 0.50 | 1.5 | 0.75 | 66.31 | 25.98 | 7.71 |
| fraction 18 | 0.40 | 1.5 | 0.60 | 64.08 | 29.11 | 6.81 |
| fraction 19 | 0.26 | 1.5 | 0.39 | 61.91 | 31.23 | 6.86 |
| fraction 20 | 0.17 | 1.5 | 0.26 | 58.82 | 32.78 | 8.41 |

The resolution of the monomer peak and the aggregate peak was determined using the program PeakFit (Seasolve Software Inc.) to be 0.90.

Example 16

Chromatography Conditions

Polypeptide: anti-IL17 antibody
Equilibration solution: 10 mM sodium citrate buffer, 10% (w/w) poly (ethylene glycol) (MW 3,500 Da), 8% (w/w) glycine adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 8% (w/w) glycine adjusted to pH 5.0, 4 column volume
Elution solution: 10 mM sodium citrate buffer, 10% (w/w) poly (ethylene glycol) (MW 3,500 Da), 8% (w/w) glycine, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 8.82 | 10.76 | 94.87 | 94.88 | 5.12 | 0 |
| flow-through | 0.00 | ~90 | 0.00 | 0 | 0 | 0 |
| fraction 1 | 0.31 | 1.5 | 0.47 | 53.77 | 0 | 46.73 |
| fraction 2 | 1.57 | 1.5 | 2.36 | 100 | 0 | 0 |
| fraction 3 | 4.68 | 1.5 | 7.02 | 100 | 0 | 0 |
| fraction 4 | 7.51 | 1.5 | 11.27 | 100 | 0 | 0 |
| fraction 5 | 9.34 | 1.5 | 14.01 | 100 | 0 | 0 |
| fraction 6 | 9.92 | 1.5 | 14.88 | 100 | 0 | 0 |
| fraction 7 | 9.60 | 1.5 | 14.40 | 100 | 0 | 0 |
| fraction 8 | 7.02 | 1.5 | 10.53 | 99.64 | 0.36 | 0 |
| fraction 9 | 3.08 | 1.5 | 4.62 | 97.59 | 2.41 | 0 |
| fraction 10 | 1.50 | 1.5 | 2.25 | 88.29 | 11.71 | 0 |
| fraction 11 | 1.33 | 1.5 | 2.00 | 70.61 | 29.39 | 0 |
| fraction 12 | 1.45 | 1.5 | 2.18 | 58.23 | 41.77 | 0 |
| fraction 13 | 1.32 | 1.5 | 1.98 | 50.02 | 49.98 | 0 |
| fraction 14 | 0.86 | 1.5 | 1.29 | 43.85 | 56.15 | 0 |
| fraction 15 | 0.47 | 1.5 | 0.71 | 42.73 | 57.27 | 0 |
| fraction 16 | 0.25 | 1.5 | 0.38 | 38.54 | 61.46 | 0 |

The resolution of the monomer peak and the aggregate peak was determined using the program PeakFit (Seasolve Software Inc.) to be 0.85.

Example 17

Chromatography Conditions

Polypeptide: anti-CSF-1R antibody
Equilibration solution: 10 mM sodium citrate buffer, 10% (w/w) poly (ethylene glycol) (MW 3,500 Da), 8% (w/w) glycine adjusted to pH 5.0, 2 column volumes
Loading: 20 g protein/l chromatography material
Wash solution: 10 mM sodium citrate buffer, 10% (w/w) poly (ethylene glycol) (MW 3,500 Da), 8% (w/w) glycine adjusted to pH 5.0, 4 column volume
Elution solution: 10 mM sodium citrate buffer, 10% (w/w) poly (ethylene glycol) (MW 3,500 Da), 8% (w/w) glycine, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.47 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 13.3 | 6.87 | 99.16 | 99.28 | 0.72 | 0 |
| flow-through | 0.00 | ~90 | 0.00 | 0 | 0 | 0 |
| fraction 1 | 0.28 | 1.5 | 0.42 | 66.36 | 0.41 | 33.23 |
| fraction 2 | 1.82 | 1.5 | 2.73 | 100 | 0 | 0 |
| fraction 3 | 5.02 | 1.5 | 7.53 | 100 | 0 | 0 |
| fraction 4 | 7.74 | 1.5 | 11.61 | 100 | 0 | 0 |
| fraction 5 | 9.05 | 1.5 | 13.58 | 100 | 0 | 0 |
| fraction 6 | 9.19 | 1.5 | 13.79 | 100 | 0 | 0 |
| fraction 7 | 8.67 | 1.5 | 13.01 | 100 | 0 | 0 |
| fraction 8 | 7.04 | 1.5 | 10.56 | 100 | 0 | 0 |
| fraction 9 | 3.82 | 1.5 | 5.73 | 99.90 | 0.10 | 0 |
| fraction 10 | 1.46 | 1.5 | 2.19 | 99.00 | 1.00 | 0 |
| fraction 11 | 0.70 | 1.5 | 1.05 | 95.61 | 4.39 | 0 |
| fraction 12 | 0.56 | 1.5 | 0.84 | 84.11 | 6.96 | 8.92 |
| fraction 13 | 0.42 | 1.5 | 0.63 | 79.56 | 8.46 | 11.99 |
| fraction 14 | 0.25 | 1.5 | 0.38 | 72.00 | 12.71 | 15.29 |

The resolution of the monomer peak and the aggregate peak was determined using the program PeakFit (Seasolve Software Inc.) to be 0.90.

Example 18

Chromatography Conditions

Polypeptide: anti-IL17 antibody
Equilibration solution: 10 mM sodium citrate buffer, 10% (w/w) poly (ethylene glycol) (MW 3,500 Da), 8% (w/w) L-proline adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 8% (w/w) L-proline adjusted to pH 5.0, 4 column volume
Elution solution: 10 mM sodium citrate buffer, 10% (w/w) poly (ethylene glycol) (MW 3,500 Da), 8% (w/w) L-proline, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 9.36 | 10.6 | 93.51 | 94.97 | 5.03 | 0 |
| flow-through | 0.00 | ~90 | 0.00 | 0 | 0 | 0 |
| fraction 1 | 0.26 | 1.5 | 0.39 | 58.65 | 0 | 41.35 |
| fraction 2 | 0.95 | 1.5 | 1.43 | 100 | 0 | 0 |
| fraction 3 | 2.58 | 1.5 | 3.87 | 100 | 0 | 0 |
| fraction 4 | 4.75 | 1.5 | 7.13 | 100 | 0 | 0 |
| fraction 5 | 6.24 | 1.5 | 9.36 | 100 | 0 | 0 |
| fraction 6 | 7.22 | 1.5 | 10.83 | 100 | 0 | 0 |
| fraction 7 | 7.96 | 1.5 | 11.94 | 100 | 0 | 0 |
| fraction 8 | 7.97 | 1.5 | 11.96 | 100 | 0 | 0 |
| fraction 9 | 7.35 | 1.5 | 11.03 | 100 | 0 | 0 |
| fraction 10 | 5.76 | 1.5 | 8.64 | 100 | 0 | 0 |
| fraction 11 | 2.89 | 1.5 | 4.34 | 98.95 | 1.05 | 0 |
| fraction 12 | 1.18 | 1.5 | 1.77 | 94.31 | 5.69 | 0 |
| fraction 13 | 0.68 | 1.5 | 1.02 | 80.42 | 19.58 | 0 |
| fraction 14 | 0.63 | 1.5 | 0.95 | 68.26 | 31.74 | 0 |
| fraction 15 | 0.72 | 1.5 | 1.08 | 50.87 | 49.13 | 0 |
| fraction 16 | 0.84 | 1.5 | 1.26 | 60.95 | 39.05 | 0 |
| fraction 17 | 0.90 | 1.5 | 1.35 | 75.25 | 24.75 | 0 |
| fraction 18 | 0.81 | 1.5 | 1.22 | 78.25 | 21.75 | 0 |
| fraction 19 | 0.59 | 1.5 | 0.89 | 79.58 | 20.42 | 0 |
| fraction 20 | 0.38 | 1.5 | 0.57 | 73.76 | 26.24 | 0 |
| fraction 21 | 0.24 | 1.5 | 0.36 | 75.45 | 24.55 | 0 |
| fraction 22 | 0.16 | 1.5 | 0.24 | 76.72 | 23.28 | 0 |

The resolution of the monomer peak and the aggregate peak was determined using the program PeakFit (Seasolve Software Inc.) to be 0.83.

Example 19

Chromatography Conditions

Polypeptide: anti-CSF-1R antibody
Equilibration solution: 10 mM sodium citrate buffer, 10% (w/w) poly (ethylene glycol) (MW 3,500 Da), 8% (w/w) L-proline adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 8% (w/w) L-proline adjusted to pH 5.0, 4 column volume
Elution solution: 10 mM sodium citrate buffer, 10% (w/w) poly (ethylene glycol) (MW 3,500 Da), 8% (w/w) L-proline, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.47 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 13.3 | 7.31 | 97.20 | 99.33 | 0.67 | 0 |
| flow-through | 0.00 | ~90 | 0.00 | 0 | 0 | 0 |
| fraction 1 | 0.51 | 1.5 | 0.77 | 67.91 | 0.38 | 31.71 |
| fraction 2 | 2.31 | 1.5 | 3.47 | 100 | 0 | 0 |
| fraction 3 | 4.90 | 1.5 | 7.35 | 100 | 0 | 0 |
| fraction 4 | 6.60 | 1.5 | 9.90 | 100 | 0 | 0 |
| fraction 5 | 7.41 | 1.5 | 11.12 | 100 | 0 | 0 |
| fraction 6 | 7.70 | 1.5 | 11.55 | 100 | 0 | 0 |
| fraction 7 | 7.87 | 1.5 | 11.81 | 100 | 0 | 0 |
| fraction 8 | 7.21 | 1.5 | 10.82 | 100 | 0 | 0 |
| fraction 9 | 6.14 | 1.5 | 9.21 | 100 | 0 | 0 |
| fraction 10 | 4.35 | 1.5 | 6.53 | 100 | 0 | 0 |
| fraction 11 | 2.13 | 1.5 | 3.20 | 99.89 | 0.11 | 0 |
| fraction 12 | 0.83 | 1.5 | 1.25 | 99.16 | 0.84 | 0 |
| fraction 13 | 0.38 | 1.5 | 0.57 | 79.11 | 5.30 | 15.59 |
| fraction 14 | 0.27 | 1.5 | 0.41 | 63.62 | 16.62 | 19.76 |
| fraction 15 | 0.24 | 1.5 | 0.36 | 46.29 | 27.44 | 26.27 |
| fraction 16 | 0.18 | 1.5 | 0.27 | 68.51 | 31.49 | 20.66 |

The resolution of the monomer peak and the aggregate peak was determined using the program PeakFit (Seasolve Software Inc.) to be 0.97.

Example 20

Chromatography Conditions

Polypeptide: anti-IL17 antibody
Equilibration solution: 10 mM sodium citrate buffer, 10% (w/w) poly (ethylene glycol) (MW 3,500 Da), 8% (w/w) Betaine adjusted to pH 5.0, 2 column volumes
Loading: 20 g protein/l chromatography material
Wash solution: 10 mM sodium citrate buffer, 10% (w/w) poly (ethylene glycol) (MW 3,500 Da), 8% (w/w) Betaine adjusted to pH 5.0, 4 column volume
Elution solution: 10 mM sodium citrate buffer, 10% (w/w) poly (ethylene glycol) (MW 3,500 Da), 8% (w/w) Betaine, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.45 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 9.24 | 10.81 | 99.86 | 94.16 | 5.84 | 0 |
| flow-through | 0.00 | ~90 | 0.00 | 0 | 0 | 0 |
| fraction 1 | 0.21 | 1.5 | 0.32 | 51.88 | 0 | 48.12 |
| fraction 2 | 0.61 | 1.5 | 0.92 | 57.58 | 0 | 42.46 |
| fraction 3 | 1.59 | 1.5 | 2.39 | 100 | 0 | 0 |
| fraction 4 | 3.25 | 1.5 | 4.88 | 100 | 0 | 0 |
| fraction 5 | 5.11 | 1.5 | 7.67 | 100 | 0 | 0 |
| fraction 6 | 6.63 | 1.5 | 9.95 | 100 | 0 | 0 |
| fraction 7 | 7.69 | 1.5 | 11.54 | 100 | 0 | 0 |
| fraction 8 | 8.26 | 1.5 | 12.39 | 100 | 0 | 0 |
| fraction 9 | 8.15 | 1.5 | 12.23 | 100 | 0 | 0 |
| fraction 10 | 7.88 | 1.5 | 11.82 | 100 | 0 | 0 |
| fraction 11 | 5.02 | 1.5 | 7.53 | 100 | 0 | 0 |
| fraction 12 | 1.91 | 1.5 | 2.87 | 95.64 | 4.36 | 0 |
| fraction 13 | 0.84 | 1.5 | 1.26 | 85.39 | 14.61 | 0 |
| fraction 14 | 0.72 | 1.5 | 1.08 | 68.77 | 31.23 | 0 |
| fraction 15 | 0.81 | 1.5 | 1.22 | 66.73 | 33.27 | 0 |
| fraction 16 | 0.89 | 1.5 | 1.34 | 64.45 | 35.55 | 0 |
| fraction 17 | 0.88 | 1.5 | 1.32 | 49.18 | 50.82 | 0 |
| fraction 18 | 0.77 | 1.5 | 1.16 | 46.31 | 53.69 | 0 |
| fraction 19 | 0.53 | 1.5 | 0.80 | 44.49 | 55.51 | 0 |
| fraction 20 | 0.34 | 1.5 | 0.51 | 35.48 | 64.52 | 0 |
| fraction 21 | 0.22 | 1.5 | 0.33 | 33.50 | 66.5 | 0 |
| fraction 22 | 0.15 | 1.5 | 0.23 | 32.72 | 67.28 | 0 |

The resolution of the monomer peak and the aggregate peak was determined using the program PeakFit (Seasolve Software Inc.) to be 0.86.

Example 21

Chromatography Conditions

Polypeptide: anti-CSF-1R antibody
Equilibration solution: 10 mM sodium citrate buffer, 10% (w/w) poly (ethylene glycol) (MW 3,500 Da), 8% (w/w) Betaine adjusted to pH 5.0, 2 column volumes
Loading: 20 g protein/1 chromatography material
Wash solution: 10 mM sodium citrate buffer, 10% (w/w) poly (ethylene glycol) (MW 3,500 Da), 8% (w/w) Betaine adjusted to pH 5.0, 4 column volume
Elution solution: 10 mM sodium citrate buffer, 10% (w/w) poly (ethylene glycol) (MW 3,500 Da), 8% (w/w) Betaine, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.47 | fraction volume [ml] | antibody amount [mg] | antibody monomer (SEC) [%] | antibody aggregate (SEC) [%] | antibody fragments (SEC) [%] |
|---|---|---|---|---|---|---|
| conditioned protein A eluate | 13.8 | 7.55 | 99.16 | 99.22 | 0.78 | 0 |
| flow-through | 0.00 | ~90 | 0.00 | 0 | 0 | 0 |
| fraction 1 | 0.33 | 1.5 | 0.50 | 71.12 | 0.40 | 28.48 |
| fraction 2 | 1.61 | 1.5 | 2.42 | 100 | 0 | 0 |
| fraction 3 | 4.31 | 1.5 | 6.47 | 100 | 0 | 0 |
| fraction 4 | 6.58 | 1.5 | 9.87 | 100 | 0 | 0 |
| fraction 5 | 7.75 | 1.5 | 11.63 | 100 | 0 | 0 |
| fraction 6 | 8.30 | 1.5 | 12.45 | 100 | 0 | 0 |
| fraction 7 | 8.40 | 1.5 | 12.60 | 100 | 0 | 0 |
| fraction 8 | 8.13 | 1.5 | 12.20 | 100 | 0 | 0 |
| fraction 9 | 7.34 | 1.5 | 11.01 | 100 | 0 | 0 |
| fraction 10 | 5.40 | 1.5 | 8.10 | 100 | 0 | 0 |
| fraction 11 | 2.61 | 1.5 | 3.92 | 99.82 | 0.18 | 0 |
| fraction 12 | 0.92 | 1.5 | 1.38 | 98.56 | 1.44 | 0 |
| fraction 13 | 0.42 | 1.5 | 0.63 | 92.33 | 7.67 | 0 |
| fraction 14 | 0.34 | 1.5 | 0.51 | 88.25 | 11.75 | 0 |
| fraction 15 | 0.32 | 1.5 | 0.48 | 85.93 | 14.07 | 0 |
| fraction 16 | 0.24 | 1.5 | 0.36 | 82.38 | 17.62 | 0 |
| fraction 17 | 0.17 | 1.5 | 0.26 | 77.09 | 22.91 | 0 |

The resolution of the monomer peak and the aggregate peak was determined using the program PeakFit (Seasolve Software Inc.) to be 0.86.

Example 22

Chromatography Conditions

Polypeptide: anti-IL 17 antibody
Equilibration solution: 10 mM sodium citrate buffer adjusted to pH 5.0, 2 column volumes
Loading: 20 g protein/1 chromatography material
Wash solution: 10 mM sodium citrate buffer, 10% (w/w) poly (ethylene glycol) (MW 400 Da), 15% (w/w) sorbitol adjusted to pH 5.0, 4 column volume
Elution solution: 10 mM sodium citrate buffer, 10% (w/w) poly (ethylene glycol) (MW 400 Da), 15% (w/w) sorbitol, comprising 750 mM sodium chloride, adjusted to pH 5.0
Elution method: linear gradient from 0% (v/v) to 100% (v/v) elution solution in 22.5 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.47 | fraction volume [ml] | antibody amount [mg] | antibody monomer (SEC) [%] | antibody aggregate (SEC) [%] |
|---|---|---|---|---|---|
| conditioned protein A eluate | 9.76 | 10.8 | 105.00 | 93.34 | 6.66 |
| flow-through | 0.00 | ~60 | 0.00 | — | — |
| fraction 1 | 3.19 | 2.0 | 6.38 | 100 | 0 |
| fraction 2 | 11.2 | 2.0 | 22.40 | 100 | 0 |
| fraction 3 | 12.2 | 2.0 | 24.40 | 100 | 0 |
| fraction 4 | 8.89 | 2.0 | 17.78 | 99.64 | 0.36 |
| fraction 5 | 5.22 | 2.0 | 10.44 | 94.65 | 5.35 |
| fraction 6 | 3.45 | 2.0 | 6.90 | 72.24 | 27.76 |
| fraction 7 | 2.33 | 2.0 | 4.66 | 44.63 | 55.37 |
| fraction 8 | 1.46 | 2.0 | 2.92 | 33.75 | 66.25 |
| fraction 9 | 0.86 | 2.0 | 1.72 | 24.38 | 75.62 |
| fraction 10 | 0.46 | 2.0 | 0.92 | 30.67 | 69.33 |
| fraction 11 | 0.27 | 2.0 | 0.54 | 51.34 | 48.66 |
| fraction 12 | 0.20 | 2.0 | 0.40 | 64.8 | 35.2 |
| fraction 13 | 0.17 | 2.0 | 0.34 | 71.58 | 28.42 |
| fraction 14 | 0.15 | 2.0 | 0.30 | 75.35 | 24.65 |

The resolution of the monomer peak and the aggregate peak was determined using the program PeakFit (Seasolve Software Inc.) to be 0.57.

Example 23

Chromatography Conditions

Polypeptide: anti-IL 17 antibody
Equilibration solution: 10 mM sodium citrate buffer adjusted to pH 5.0, 2 column volumes
Loading: 20 g protein/1 chromatography material
Wash solution: 10 mM sodium citrate buffer, 10% (w/w) poly (ethylene glycol) (MW 10,000 Da), 15% (w/w) sorbitol adjusted to pH 5.0, 4 column volume
Elution solution: 10 mM sodium citrate buffer, 10% (w/w) poly (ethylene glycol) (MW 10,000 Da), 15% (w/w) sorbitol, comprising 750 mM sodium chloride, adjusted to pH 5.0
Elution method: linear gradient from 0% (v/v) to 100% (v/v) elution solution in 30 column volumes The peak containing the antibody was collected in 3 ml fractions, which were analyzed for monomer and aggregate content as well as for CHO host cell protein content and CHO host cell DNA content. The result of the analysis is presented in the following Table.

TABLE

| sample | concentration (UV280) [mg/ml] E = 1.47 | fraction volume [ml] | antibody amount [mg] | antibody monomer (SEC) [%] | antibody aggregate (SEC) [%] |
|---|---|---|---|---|---|
| conditioned protein A eluate | 9.06 | 10.5 | 95.13 | 93.30 | 6.70 |
| flow-through | 0.00 | ~100 | 0.00 | — | — |
| fraction 1 | 0.27 | 2.0 | 0.54 | 100 | 0 |
| fraction 2 | 0.56 | 2.0 | 1.12 | 100 | 0 |
| fraction 3 | 1.04 | 2.0 | 2.08 | 100 | 0 |
| fraction 4 | 1.59 | 2.0 | 3.18 | 100 | 0 |
| fraction 5 | 2.09 | 2.0 | 4.18 | 100 | 0 |
| fraction 6 | 2.46 | 2.0 | 4.92 | 100 | 0 |
| fraction 7 | 2.78 | 2.0 | 5.56 | 100 | 0 |
| fraction 8 | 3.03 | 2.0 | 6.06 | 100 | 0 |
| fraction 9 | 3.06 | 2.0 | 6.12 | 100 | 0 |
| fraction 10 | 3.15 | 2.0 | 6.30 | 100 | 0 |
| fraction 11 | 3.06 | 2.0 | 6.12 | 100 | 0 |
| fraction 12 | 3.04 | 2.0 | 6.08 | 100 | 0 |
| fraction 13 | 3.21 | 2.0 | 6.42 | 100 | 0 |
| fraction 14 | 2.85 | 2.0 | 5.70 | 100 | 0 |
| fraction 15 | 2.52 | 2.0 | 5.04 | 99.46 | 0.54 |
| fraction 16 | 1.07 | 2.0 | 2.14 | 92.89 | 7.11 |
| fraction 17 | 0.48 | 2.0 | 0.96 | 74.81 | 25.19 |
| fraction 18 | 0.33 | 2.0 | 0.66 | 49.32 | 50.68 |
| fraction 19 | 0.30 | 2.0 | 0.60 | 22.75 | 77.25 |
| fraction 20 | 0.28 | 2.0 | 0.56 | 25.32 | 74.68 |
| fraction 21 | 0.27 | 2.0 | 0.54 | 17.5 | 82.5 |
| fraction 22 | 0.28 | 2.0 | 0.56 | 17.29 | 82.71 |
| fraction 23 | 0.28 | 2.0 | 0.56 | 13.47 | 86.53 |
| fraction 24 | 0.28 | 2.0 | 0.56 | 17.42 | 82.58 |
| fraction 25 | 0.27 | 2.0 | 0.54 | 14.09 | 85.91 |
| fraction 26 | 0.27 | 2.0 | 0.54 | 15.36 | 84.64 |
| fraction 27 | 0.24 | 2.0 | 0.48 | 11.57 | 88.43 |
| fraction 28 | 0.23 | 2.0 | 0.46 | 13.01 | 86.99 |
| fraction 29 | 0.19 | 2.0 | 0.38 | 12.61 | 87.39 |
| fraction 30 | 0.14 | 2.0 | 0.28 | 13.29 | 86.71 |

The resolution of the monomer peak and the aggregate peak was determined using the program PeakFit (Seasolve Software Inc.) to be 0.70.

Example 24

Chromatography Conditions

Polypeptide: Anti-Ang2/VEGF antibody
Exchange material: Poros 50HS
Column: 11 mm internal diameter, 250 mm length, 23 ml volume
Flow rate: 90 cm/h
Equilibration solution: 40 mM sodium phosphate buffer, adjusted to pH 5.0, 3 column volumes
Loading: 20 g protein/1 chromatography material
Wash solution: 40 mM sodium phosphate buffer, adjusted to pH 5.0, 3 column volumes
Elution solution: 40 mM sodium phosphate buffer, adjusted to pH 7.5
Elution method: linear gradient from 0% (v/v) to 100% (v/v) elution solution in 12 column volumes The conditioned anion exchange eluate was applied to a chromatography column containing the cation exchange chromatography material. After the loading step at a flow rate of 90 cm/h the column was washed with wash solution (3 column volume). The antibody was recovered with a linear gradient elution method, whereby the pH value was varied (increased) from 5.0 to 7.5.

The ¾ antibody "co-elutes" with the antibody monomer and two ¾ antibody peaks are detected.

Example 25

Chromatography Conditions

Polypeptide: Anti-Ang2/VEGF antibody
Exchange material: Poros 50HS
Column: 11 mm internal diameter, 250 mm length, 23 ml volume
Flow rate: 90 cm/h
Equilibration solution: 40 mM sodium phosphate buffer, 5% PEG 4000, adjusted to pH 5.0, 3 column volumes
Loading: 20 g protein/1 chromatography material
Wash solution: 40 mM sodium phosphate buffer, 5% PEG 4000, adjusted to pH 5.0, 3 column volumes
Elution solution: 40 mM sodium phosphate buffer, 5% PEG 4000, adjusted to pH 7.5
Elution method: linear gradient from 0% (v/v) to 100% (v/v) elution solution in 12 column volumes The conditioned anion exchange eluate was applied to a chromatography column containing the cation exchange chromatography material. After the loading step at a flow rate of 90 cm/h the column was washed with wash solution (3 column volume). The antibody was recovered with a linear gradient elution method, whereby the pH value was varied (increased) from 5.0 to 7.5.

Example 26

Chromatography Conditions

Polypeptide: Anti-Ang2/VEGF antibody
Exchange material: Poros 50HS
Column: 11 mm internal diameter, 250 mm length, 23 ml volume
Flow rate: 90 cm/h
Equilibration solution: 40 mM sodium phosphate buffer, adjusted to pH 5.0, 3 column volumes
Loading: 20 g protein/1 chromatography material Wash solution: 40 mM sodium phosphate buffer, 10% PEG 4000, 8% glycine, adjusted to pH 5.0, 3 column volumes Elution solution: 40 mM sodium phosphate buffer, 10% PEG 4000, 8% glycine, adjusted to pH 7.5

Elution method: linear gradient from 0% (v/v) to 100% (v/v) elution solution in 12 column volumes The conditioned anion exchange eluate was applied to a chromatography column containing the cation exchange chromatography material. After the loading step at a flow rate of 90 cm/h the column was washed with wash solution (3 column volume). The antibody was recovered with a linear gradient elution method, whereby the pH value was varied (increased) from 5.0 to 7.5.

In FIG. 6 the distribution of antibody in monomeric form, ¾ antibody fragment and antibody in aggregated form over the collected fractions of the cation exchange chromatography of the anti-Ang2/VEGF antibody on the cation exchange chromatography material is shown. The antibody in monomeric form and the antibody in aggregated form and the ¾ antibody fragment are separated.

The invention claimed is:

1. A method for producing an antibody of the IgG class in monomeric form comprising the following steps:

applying a first solution that optionally comprises poly (ethylene glycol) and sorbitol to a cation exchange chromatographic material, thereby equilibrating the material;

applying a solution comprising an antibody of the IgG class to the equilibrated cation exchange chromatography material, thereby loading the chromatography material;

applying a solution comprising poly (ethylene glycol) having a concentration of about 10% by weight and sorbitol having a concentration of from 5% to 20% by weight to the cation exchange chromatographic material, thereby separating the antibody of the IgG class in monomeric form from the antibody in aggregate form and obtaining the antibody in monomeric form.

2. A method for producing an antibody of the IgG class preparation with reduced host cell protein content comprising the following steps:

applying a first solution that optionally comprises poly (ethylene glycol) and sorbitol to a cation exchange chromatographic material, thereby equilibrating the material;

applying a solution comprising an antibody of the IgG class to the equilibrated cation exchange chromatography material, thereby loading the chromatography material;

applying a solution comprising poly (ethylene glycol) having a concentration of about 10% by weight and sorbitol having a concentration of from 5% to 20% by weight to the cation exchange chromatographic material, thereby separating the antibody of the IgG class in monomeric form with reduced host cell protein content from the antibody in aggregate form and obtaining the antibody in monomeric form with reduced host cell protein content.

3. The method according to claim 1, characterized in that the poly (ethylene glycol) has a molecular weight of about 3,500 Da+/−20%.

4. The method according to claim 1, characterized in that the monomeric antibody has a molecular weight of from 100 kDa to 200 kDa.

* * * * *